United States Patent
Zhang

(10) Patent No.: US 12,318,482 B2
(45) Date of Patent: *Jun. 3, 2025

(54) EXOSOMAL COMPOSITIONS AND METHODS FOR THE TREATMENT OF DISEASE

(71) Applicant: University of Louisville Research Foundation, Inc., Louisville, KY (US)

(72) Inventor: Huang-Ge Zhang, Louisville, KY (US)

(73) Assignee: University of Louisville Research Foundation, Inc., Louisville, KY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/214,335

(22) Filed: Jun. 26, 2023

(65) Prior Publication Data
US 2023/0355525 A1  Nov. 9, 2023

Related U.S. Application Data

(63) Continuation of application No. 18/129,593, filed on Mar. 31, 2023, which is a continuation of application No. 16/359,618, filed on Mar. 20, 2019, now abandoned, which is a continuation of application No. 15/917,151, filed on Mar. 9, 2018, now abandoned, which is a continuation of application No. 14/107,691, filed on Dec. 16, 2013, now abandoned, which is a continuation of application No. 13/576,907, filed as application No. PCT/US2011/023747 on Feb. 4, 2011, now abandoned.

(60) Provisional application No. 61/424,875, filed on Dec. 20, 2010, provisional application No. 61/301,939, filed on Feb. 5, 2010.

(51) Int. Cl.
| | | |
|---|---|---|
| *A61K 9/127* | (2025.01) |
| *A61K 31/05* | (2006.01) |
| *A61K 31/12* | (2006.01) |
| *A61K 31/282* | (2006.01) |
| *A61K 31/337* | (2006.01) |
| *A61K 31/353* | (2006.01) |
| *A61K 31/475* | (2006.01) |
| *A61K 31/513* | (2006.01) |
| *A61K 31/575* | (2006.01) |
| *A61K 31/704* | (2006.01) |
| *A61K 33/243* | (2019.01) |
| *A61K 45/06* | (2006.01) |

(52) U.S. Cl.
CPC .............. *A61K 9/127* (2013.01); *A61K 31/05* (2013.01); *A61K 31/12* (2013.01); *A61K 31/282* (2013.01); *A61K 31/337* (2013.01); *A61K 31/353* (2013.01); *A61K 31/475* (2013.01); *A61K 31/513* (2013.01); *A61K 31/575* (2013.01); *A61K 31/704* (2013.01); *A61K 33/243* (2019.01); *A61K 45/06* (2013.01)

(58) Field of Classification Search
None
See application file for complete search history.

(56) References Cited

U.S. PATENT DOCUMENTS

2009/0299045 A1   12/2009   Richards et al.

FOREIGN PATENT DOCUMENTS

| WO | WO-2005004925 A1 * | 1/2005 | ....... A61K 47/48776 |
| WO | 2007126386 A1 | 11/2007 | |

OTHER PUBLICATIONS

Regente, M. et al. 2009. Vesicular fractions of sunflower apoplastic fluids are associated with potential exosome marker proteins. FEBS Letters 583: 3363-3366; specif. pp. 3363, 3364, 3365, 3366 (Year: 2009).*

Jacob, J.K. et al. 2008. Physico-chemical characteristics of nanovesicle-carbohydrate complexes in grape juice concentrate. Journal of Agricultural and Food Chemistry 56: 1305-1315; specif. pp. 1305, 1306, 1312, 1314 (Year: 2008).*

Non-Final Office Action received in connection with U.S. Appl. No. 18/129,593, dated May 24, 2024, 26 pages.

Kim, S.H. et al. 2007. Effective treatment of inflammatory diesease models with exosomes derived from dendritic cells genetically modified to express IL-4. Journal of Immunology 179: 2242-2249; specif. pp. 2242, 2243, 2248, 2249 (Year: 2007).

* cited by examiner

*Primary Examiner* — Adam Weidner
*Assistant Examiner* — Sharon M. Papciak
(74) *Attorney, Agent, or Firm* — Meunier Carlin & Curfman LLC

(57) ABSTRACT

An exosomal composition is provided that includes a therapeutic agent encapsulated by an exosome. The therapeutic agent can be a phytochemical agent, a chemotherapeutic agent, or a Stat3 inhibitor. Pharmaceutical compositions that contain the exosomal compositions are also provided. Methods for treating an inflammatory disease or a cancer are further provided and include administering an effective amount of an exosomal composition to a subject in need thereof to thereby treat the inflammatory disorder or the cancer.

13 Claims, 19 Drawing Sheets

EXOSOMAL COMPOSITIONS AND METHODS FOR THE TREATMENT OF DISEASE

CROSS REFERENCE TO RELATED APPLICATIONS

This application is a continuation of U.S. application Ser. No. 16/359,618, filed Mar. 20, 2019, which is a continuation of U.S. application Ser. No. 15/917,151, filed Mar. 9, 2018, which is a continuation of U.S. application Ser. No. 14/107,691, filed Dec. 16, 2013, which is a continuation of U.S. application Ser. No. 13/576,907, filed Aug. 2, 2012, and which is a 371 national stage application of PCT International Patent Application Serial No. PCT/US2011/023747, filed Feb. 4, 2011, and which claims priority from U.S. Provisional Application Ser. No. 61/424,875, filed Dec. 20, 2010, and U.S. Provisional Application Ser. No. 61/301,939, filed Feb. 5, 2010, the entire disclosure of each of which is incorporated herein reference in its entirety.

GOVERNMENT INTEREST

This invention was made with government support under grant numbers R01CA137037 and R01AT004294 awarded by National Institutes of Health. The government has certain rights in the invention.

TECHNICAL FIELD

The presently disclosed subject matter relates to exosomal compositions and methods of using the same for the treatment of disease. In particular, the presently disclosed subject matter relates to exosomal compositions that comprise therapeutic agents encapsulated by an exosome and are useful in the treatment of inflammatory disorders and cancer.

BACKGROUND

Fifty years ago, the nanotechnology concept was initially proposed and, in 2000, the National Nanotechnology Institute (NNI) defined nanotechnology as "[t]he understanding and control of matter at dimensions of roughly 1 to 100 nm, where unique phenomena enable novel applications." The application of nanoscale or nanostructured material in medicine has since been extended to objects with sizes of up to 1000 nm and numerous nanoparticle materials, such as polymers, liposomes, metals, and carbon nanotubes, are now being examined as potential therapeutic agent delivery vectors. For instance, researchers have developed or are currently developing methods by which small molecule drugs, peptides, proteins, DNA and even siRNA molecules are packed into nanoparticles and then used to treat multiple fungal infections, inflammatory diseases, bone defects, and cancers.

Despite ongoing research into the use of nanoparticles as therapeutic agent-delivery vectors, however, in the fight against inflammatory disorders and cancers, localized drug delivery and specific targeting are two major problems researchers and clinicians must still confront. Indeed, one of the most challenging issues in anti-cancer and anti-inflammatory therapy continues to be achieving delivery of therapeutic agents to specific inflammatory cells and tumor cells in vivo and then, upon delivery, having the particular therapeutic agent retain its activity. For example, in spite of the development of therapeutic agents that preferentially target inflammatory and cancer cells without harming normal tissues, the delivery of these agents to the brain continues to be a major challenge because of difficulty in penetrating the blood-brain barrier (51-56). Indeed, the further development of many therapeutic agents has been abandoned because sufficient therapeutic agent levels in the brain could not be achieved via the systemic circulation. Intranasal delivery has previously provided a noninvasive method for delivering therapeutic agents to the brain in some instances, but the quantities of therapeutic agents that are able to be administered via that route and that are transported directly from nose-to-brain continue to be very low (61-65).

Recently, efforts have been made to confront these problems via the further development of nanoparticle-therapeutic agent delivery systems. To date, however, the development of an efficient and specific nanoparticle-therapeutic agent delivery system has yet to be produced that is able to locally deliver the agent to the target cells and tissues while retaining a sufficient biological activity.

SUMMARY

The presently disclosed subject matter meets some or all of the above-identified needs, as will become evident to those of ordinary skill in the art after a study of information provided in this document.

This Summary describes several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter includes exosomal compositions and methods of using the exosomal compositions for the treatment of disease. More specifically, the presently disclosed subject matter relates to exosomal compositions where one or more therapeutic agents are encapsulated within an exosome and are used to treat inflammatory disorders or cancers.

In some embodiments of the presently disclosed subject matter, an exosomal composition is provided where an exosome encapsulates a therapeutic agent that is selected from a phytochemical agent, a chemotherapeutic agent, and a Stat3 inhibitor. In some embodiments, the therapeutic agent is a phytochemical agent selected from the group consisting of curcumin, resveratrol, baicalein, equol, fisetin, and quercetin. In other embodiments, the therapeutic agent is a Stat3 inhibitor, such as JSI-124. In further embodiments, the therapeutic agent is a chemotherapeutic agent that, in certain embodiments, is selected from the group consisting of retinoic acid, 5-fluorouracil, vincristine, actinomycin D, adriamycin, cisplatin, docetaxel, doxorubicin, and taxol.

In some embodiments, the exosomal compositions that are produced in accordance with the presently disclosed subject matter make use of exosomes that are first isolated from a cell before the exosomes are then used to encapsulate a therapeutic agent of interest. In some embodiments, the exosomes are first isolated from a cancer cell, which, in some embodiments, is selected from a lymphoma cell, an adenocarcinoma cell, or a breast cancer cell. In some embodiments, the exosomes are fruit-derived exosomes, such as grape exosomes.

Further provided, in some embodiments, are pharmaceutical compositions comprising an exosomal composition of the presently disclosed subject matter. In some embodiments, a pharmaceutical composition is provided that comprises an exosomal composition of the presently disclosed subject matter and a pharmaceutically acceptable vehicle, carrier, or excipient.

Still further provided, in some embodiments of the presently disclosed subject matter, are methods for treating an inflammatory disorder. In some embodiments, a method for treating an inflammatory disorder is provided that comprises administering to a subject in need thereof an effective amount of an exosomal composition of the presently disclosed subject matter. In some embodiments of the methods for treating an inflammatory disorder, the therapeutic agent is selected from a phytochemical agent and a Stat3 inhibitor. In some embodiments, the exosomal composition, which includes the phytochemical agent or the Stat3 inhibitor encapsulated in an exosome, is administered intranasally.

In some embodiments of the presently disclosed subject methods for treating an inflammatory disorder, the inflammatory disorder is a brain-related inflammatory disorder. In some embodiments, the inflammatory disorder is an autoimmune disease such as, in some embodiments, lupus, rheumatoid arthritis, or autoimmune encephalomyelitis. In some embodiments, administering the exosomal composition as part of a method for treating an inflammatory disorder reduces an amount of an inflammatory cytokine in a subject. In some embodiments, the inflammatory cytokine is selected from the group consisting of interleukin-1ß, tumor necrosis factor-α, and interleukin-6.

In yet further embodiments of the presently disclosed subject matter, methods for treating a cancer are provided. In some embodiments, a method for treating a cancer is provided that comprises administering to a subject in need thereof an effective amount of an exosomal composition of the presently disclosed subject matter. In some embodiments of the methods for treating a cancer, the therapeutic agent encapsulated by an exosome is selected from a phytochemical agent, a chemotherapeutic agent, and a Stat3 inhibitor.

In some embodiments, the methods for treating a cancer disclosed herein are used to treat a skin cancer, a head and neck cancer, a colon cancer, a breast cancer, a brain cancer, and a lung cancer. In some embodiments, the cancer is a brain cancer that, in some embodiments, comprises a glioma. In some embodiments, the exosomal compositions of the presently disclosed subject matter are used to treat the cancer by administering the exosomal compositions intranasally, orally, or intratumorally.

Further advantages of the presently disclosed subject matter will become evident to those of ordinary skill in the art after a study of the description, Figures, and non-limiting Examples in this document.

DESCRIPTION OF EXEMPLARY EMBODIMENTS

Figure 1A:
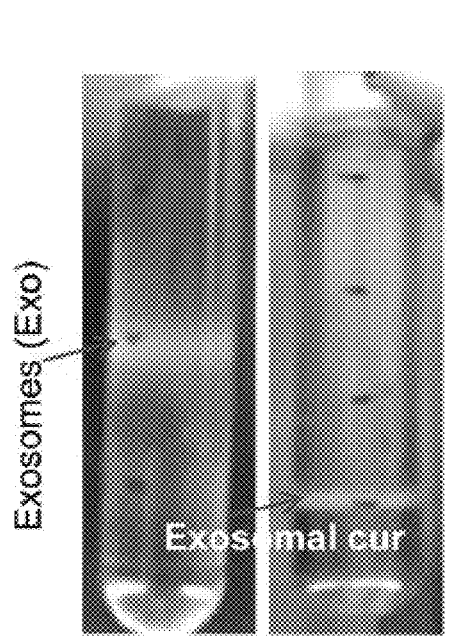
FIG. 1A includes photographs showing the results of sucrose gradient centrifugation procedures used to purify exosomes encapsulating curcumin (i.e., exosomal curcumin), where the left image shows the original exosomes without the encapsulated therapeutic agent as a weak band and the right image shows the exosomal curcumin as a darker band appearing between higher concentration sucrose gradients.

The details of one or more embodiments of the presently disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. Additionally, while the following terms are believed to be well understood by one of ordinary skill in the art, definitions are set forth to facilitate explanation of the presently disclosed subject matter.

Unless defined otherwise, all technical and scientific terms used herein have the same meaning as commonly understood by one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments #1%, in some embodiments ±0.5%, and in some embodiments ±0.1% from the specified amount, as such variations are appropriate to perform the disclosed method. As also used herein, ranges can be expressed as from "about" one particular value, and/or to "about" another particular value. It is also understood that there are a number of values disclosed herein, and that each value is also herein disclosed as "about" that particular value in addition to the value itself.

For example, if the value "10" is disclosed, then "about 10" is also disclosed. It is also understood that each unit between two particular units are also disclosed. For example, if 10 and 15 are disclosed, then 11, 12, 13, and 14 are also disclosed.

Exosomes are naturally existing nanoparticles that are secreted endogenously by many types of in vitro cell cultures and in vivo cells, and are commonly found in vivo in body fluids, such as blood, urine and malignant ascites. Exosomes are cup-like multivesicular bodies (MVBs) varying in size between 30-100 nm (12). MVBs are specialized endosomes in the endocytosis pathway of cells and are formed by inward budding and scission of vesicles from the limiting membranes into the endosomal lumen (13). During the formation of MVBs, transmembrane and peripheral membrane proteins are absorbed into the vesicle membrane, and at the same time, cytosolic components are also embedded in the vesicles. As this process progresses, the MVBs ultimately fuse with the cellular membrane, triggering the release of the exosomes from the cells.

During this process, unwanted molecules are eliminated from cells. However, cytosolic and plasma membrane proteins are also incorporated during this process into the exosomes, resulting in exosomes having particle size properties, lipid bilayer functional properties, and other unique functional properties that allow the exosomes to potentially function as effective nanoparticle carriers of therapeutic agents. In this regard, it has now been discovered that exosomes can be used as part of a specific nanoparticle-therapeutic agent delivery system that is able to deliver a therapeutic agent to target cells and tissues, while also retaining the biological activity of the therapeutic agents. In particular, it has been observed that the formation of exosome-therapeutic agent complexes results in an increase in the solubility and stability of the therapeutic agents as well as an increase in their bioavailability, all of which have been major obstacles in the treatment of inflammatory disorders and cancers.

The presently disclosed subject matter thus relates to exosomal compositions that include therapeutic agents and are useful in the treatment of various diseases, including inflammatory disorders and cancer. In some embodiments of the presently disclosed subject matter, an exosomal composition is provided that comprises a therapeutic agent selected from a phytochemical agent, a chemotherapeutic agent, a Stat3 inhibitor, or combinations thereof. In some embodiments, the therapeutic agent is encapsulated by an exosome to thereby provide an exosomal composition that displays increased in vitro and in vivo solubility, stability, and bioavailability as compared to the free (i.e., non-encapsulated or unbound) therapeutic agent.

The phrase "encapsulated by an exosome," or grammatical variations thereof is used interchangeably herein with the phrase "exosomal therapeutic agent" or "exosomal composition" to refer to exosomes whose lipid bilayer surrounds a therapeutic agent. For example, a reference to "exosomal curcumin" refers to an exosome whose lipid bilayer encapsulates or surrounds an effective amount of curcumin.

In some embodiments, the encapsulation of various therapeutic agents within exosomes can be achieved by first mixing the one or more of the phytochemical agents, Stat3 inhibitors, or chemotherapeutic agents with isolated exosomes in a suitable buffered solution, such as phosphate-buffered saline (PBS). After a period of incubation sufficient to allow the therapeutic agent to become encapsulated during the incubation period, the exosome/therapeutic agent mixture is then subjected to a sucrose gradient (e.g., and 8, 30, 45, and 60% sucrose gradient) to separate the free therapeutic agent from the therapeutic agents encapsulated within the exosomes, and a centrifugation step to isolate the exosomes. After this centrifugation step, the exosomal therapeutic agents are seen as a band in the sucrose gradient such that they can then be collected, washed, and dissolved in a suitable solution for use as described herein below.

As noted, in some embodiments, the therapeutic agent is a phytochemical agent. As used herein, the term "phytochemical agent" refers to a non-nutritive plant-derived compound, or an analog thereof. Examples of phytochemical agents include, but are not limited to compounds such as monophenols; flavonoids, such as flavonols, flavanones, flavones, flavan-3-ols, anthocyanins, anthocyanidins, isoflavones, dihydroflavonols, chalcones, and coumestans; phenolic acids; hydroxycinnamic acids; lignans; tyrosol esters; stillbenoids; hydrolysable tannins; carotenoids, such as carotenes and xanthophylls; monoterpenes; saponins; lipids, such as phytosterols, tocopherols, and omega-3,6,9 fatty acids; diterpenes; triterpinoids; betalains, such as betacyanins and betaxanthins; dithiolthiones; thiosulphonates; indoles; and glucosinolates. As another example of a phytochemical agent disclosed herein, the phytochemical agent can be an analog of a plant-derived compound, such as oltipraz, which is an analog of 1,2-dithiol-3-thione, a compound that is found in many cruciferous vegetables.

In some embodiments of the presently disclosed subject matter, the therapeutic agent is a phytochemical agent selected from curcumin resveratrol, baicalein, equol, fisetin, and quercetin. In some embodiments, the phytochemical agent is curcumin. Curcumin is a pleiotropic natural polyphenol with anti-inflammatory, anti-neoplastic, anti-oxidant and chemopreventive activity, with these activities having been identified at both the protein and molecular levels (14, 15). Nevertheless, limited progress has been reported with respect to the therapeutic use of curcumin as curcumin is insoluble in aqueous solvents and is relatively unstable. In addition, curcumin is known to have a low systemic bioavailability after oral dosing, which further limits its usage and clinical efficacy. It has been determined, however, that by encapsulating curcumin in exosomes, not only can the solubility of curcumin be increased, but the encapsulation of the curcumin within the exosomes protects the curcumin from degradation and also increases the bioavailability of the exosomal curcumin.

As also noted herein above, in some embodiments of the presently disclosed subject matter, the therapeutic agent that is encapsulated within the exosome is a chemotherapeutic agent. Examples of chemotherapeutic agents that can be used in accordance with the presently disclosed subject matter include, but are not limited to, platinum coordination compounds such as cisplatin, carboplatin or oxalyplatin; taxane compounds, such as paclitaxel or docetaxel; topoisomerase I inhibitors such as camptothecin compounds for example irinotecan or topotecan; topoisomerase II inhibitors such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example VELCADE® (Millennium Pharmaceuticals, Cambridge, MA); or YONDELIS® (Johnson & Johnson, New Brunswick, NJ). In some embodiments, the chemotherapeutic agent that is encapsulated by an exosome in accordance with the presently disclosed subject matter is selected from retinoic acid, 5-fluorouracil, vincristine, actinomycin D, adriamycin, cisplatin, docetaxel, doxorubicin, and taxol.

As further noted, in some embodiments, the therapeutic agent is a signal transducer and activator of transcription 3 (Stat3) inhibitor. "Stat3" or "Signal Transducer and Activator of Transcription 3" is a transcription factor encoded by the STAT3 gene and, in response to cytokines or growth factors, is known to become phosphorylated and to then translocate to the nucleus of cells where it mediates the expression of a variety of genes in response to various stimuli, and thus plays a key role in a number of cellular processes including cell growth and apoptosis. In this regard, the term "Stat3 inhibitor" is used herein to refer to any chemical compound or protein that prevents or otherwise reduces the activity of Stat3 including, but not limited to, chemical compounds or proteins that prevent or reduce the transcriptional activity of Stat3, and chemical compounds or proteins that prevent or reduce the activation of Stat3 by preventing its activation (e.g., the phosphorylation and/or translocation of Stat3 to the nucleus of a cell). A number of Stat3 inhibitors are known to those skilled in the art including, but not limited to, the PIAS3 protein, Stattin, or JSI-124, which is also referred to as curcurbitacin I. In some embodiments of the presently disclosed subject matter, the Stat3 inhibitor that is encapsulated within the exosome is JSI-124.

The exosomes used to produce the exosomal compositions of the presently disclosed subject matter can be obtained from a variety of sources using methods known to those of ordinary skill in the art. The term "isolated," when used in the context of an exosome isolated from a cell, refers to an exosome that, by the hand of man, exists apart from its native environment and is therefore not a product of nature. For example, in some embodiments, the exosomes are isolated from the juices of fruit (e.g., grape, grapefruit, and tomatoes). As another example, in some embodiments, the exosomes are isolated from cells by collecting cell culture supernatants and then purifying the exosomes from the supernatants using known differential centrifugation techniques to isolate exosomes (see, e.g., Liu C, Yu S, Zinn K. et al. Murine mammary carcinoma exosomes promote tumor growth by suppression of NK cell function. J. Immunol. 176(3), 1375-1385 (2006)). As such, in some embodiments, the exosomes that are used in accordance with the presently disclosed subject matter are isolated from a cell. In some embodiments, the cell is a cultured cell, that is, a cell propagated ex vivo in culture media. In some embodiments, the culture cell can be immortalized to facilitate continuous propagation. In some embodiments, the cell is a cancer cell, such as for example a cancer cell originally isolated from a tumor and then propagated in culture, as is generally known in the art. In some embodiments, the cancer cell can be a lymphoma cell, a breast cancer cell, or an adenocarcinoma cell.

In some embodiments of the presently disclosed subject matter, the exosomal compositions of the presently disclosed subject matter specifically bind to a target cell or tissue. Applicants have discovered that exosomes released from different types of cells (i.e., derived from different cells) with different levels of activation (e.g. proliferating vs. non-proliferating) exhibit tissue- and/or cell-specific in vivo tropism, which can advantageously be utilized to direct the exosomes and the exosomal compositions to a specific cell or tissue. For example, in some embodiments, the exosome used to produce an exosomal composition of the presently disclosed subject matter is derived from a T lymphocyte and specifically binds $CD11b^+Gr1^+$ myeloid cells.

In some embodiments of the presently disclosed subject matter, a pharmaceutical composition is provided that comprises an exosomal composition disclosed herein and a pharmaceutical vehicle, carrier, or excipient. In some embodiments, the pharmaceutical composition is pharmaceutically-acceptable in humans. Also, as described further below, the pharmaceutical composition can be formulated as a therapeutic composition for delivery to a subject in some embodiments.

A pharmaceutical composition as described herein preferably comprises a composition that includes pharmaceutical carrier such as aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. The pharmaceutical compositions used can take such forms as suspensions, solutions or emulsions in oily or aqueous vehicles, and can contain formulatory agents such as suspending, stabilizing and/or dispersing agents. Additionally, the formulations can be presented in unit-dose or multi-dose containers, for example sealed ampoules and vials, and can be stored in a frozen or freeze-dried or room temperature (lyophilized) condition requiring only the addition of sterile liquid carrier immediately prior to use.

In some embodiments, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone, hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399, 359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of capsules, tablets or lozenges formulated in conventional manner.

Various liquid and powder formulations can also be prepared by conventional methods for inhalation into the lungs of the subject to be treated or for intranasal administration into the nose and sinus cavities of a subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

The compositions can also be formulated as a preparation for implantation or injection. Thus, for example, the compositions can be formulated with suitable polymeric or hydrophobic materials (e.g., as an emulsion in an acceptable oil) or ion exchange resins, or as sparingly soluble derivatives (e.g., as a sparingly soluble salt).

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the present invention and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the composition can be prepared and administered as a suspension in an aqueous base or a pharmaceutically-acceptable oil base, such as an ester of a long chain fatty acid, (e.g., ethyl oleate).

In addition to the formulations described above, the exosomal therapeutic agents of the present invention can also be formulated as rectal compositions, such as suppositories or retention enemas, e.g., containing conventional suppository bases such as cocoa butter or other glycerides. Further, the exosomal compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

Further provided, in some embodiments of the presently disclosed subject matter, are methods for treating an inflammatory disorder. In some embodiments, a method for treating an inflammatory disorder is provided that comprises administering to a subject in need thereof an effective amount of an exosomal composition of the presently disclosed subject matter. In some embodiments of the presently disclosed methods of treating an inflammatory disorder, the therapeutic agent encapsulated by an exosome is a phytochemical agent and/or a Stat-3 inhibitor.

As used herein, the terms "treatment" or "treating" relate to any treatment of a condition of interest (e.g., an inflammatory disorder or a cancer), including but not limited to prophylactic treatment and therapeutic treatment. As such, the terms "treatment" or "treating" include, but are not limited to: preventing a condition of interest or the development of a condition of interest; inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

As used herein, the term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, micro-organisms, tissue necrosis, cancer, or other agents or conditions.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories. Exemplary inflammatory disorders include, but are not limited to atherosclerosis; arthritis; inflammation-promoted cancers; asthma; autoimmune uveitis; adoptive immune response; dermatitis; multiple sclerosis; diabetic complications; osteoporosis; Alzheimer's disease; cerebral malaria; hemorrhagic fever; autoimmune disorders; and inflammatory bowel disease. In some embodiments, the inflammatory disorder is an autoimmune disorder that, in some embodiments, is selected from lupus, rheumatoid arthritis, and autoimmune encephalomyelitis.

In some embodiments, the inflammatory disorder is a brain-related inflammatory disorder. The term "brain-related inflammatory" disorder is used herein to refer to a subset of inflammatory disorders that are caused, at least in part, or originate or are exacerbated, by inflammation in the brain of a subject. It has been determined that the exosomal compositions of the presently disclosed subject matter are particularly suitable for treating such disorders as those compositions are able to cross the blood-brain barrier and effectively be used to deliver the therapeutic agents (e.g., curcumin or JSI-124) to the brain of a subject.

For administration of a therapeutic composition as disclosed herein (e.g., an exosome encapsulating a therapeutic agent), conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

Suitable methods for administering a therapeutic composition in accordance with the methods of the presently disclosed subject matter include, but are not limited to, systemic administration, parenteral administration (including intravascular, intramuscular, and/or intraarterial administration), oral delivery, buccal delivery, rectal delivery, subcutaneous administration, intraperitoneal administration, inhalation, intratracheal installation, surgical implantation, transdermal delivery, local injection, intranasal delivery, and hyper-velocity injection/bombardment. Where applicable, continuous infusion can enhance drug accumulation at a target site (see, e.g., U.S. Pat. No. 6,180,082).

Regardless of the route of administration, the compositions of the presently disclosed subject matter are typically administered in amount effective to achieve the desired response. As such, the term "effective amount" is used herein to refer to an amount of the therapeutic composition (e.g., an exosome encapsulating a therapeutic agent, and a pharmaceutically vehicle, carrier, or excipient) sufficient to produce a measurable biological response (e.g., a decrease in inflammation). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

For additional guidance regarding formulation and dose, see U.S. Pat. Nos. 5,326,902; 5,234,933; PCT International Publication No. WO 93/25521; Berkow et al., (1997) The Merck Manual of Medical Information, Home ed. Merck Research Laboratories, Whitehouse Station, New Jersey; Goodman et al., (1996) Goodman & Gilman's the Pharmacological Basis of Therapeutics, 9th ed. McGraw-Hill Health Professions Division, New York; Ebadi, (1998) CRC Desk Reference of Clinical Pharmacology. CRC Press, Boca Raton, Florida; Katzung, (2001) Basic & Clinical Pharmacology, 8th ed. Lange Medical Books/McGraw-Hill Medical Pub. Division, New York; Remington et al., (1975) Remington's Pharmaceutical Sciences, 15th ed. Mack Pub. Co., Easton, Pennsylvania; and Speight et al., (1997) Avery's Drug Treatment: A Guide to the Properties, Choice, Therapeutic Use and Economic Value of Drugs in Disease Management, 4th ed. Adis International, Auckland/Philadelphia; Duch et al., (1998) *Toxicol. Lett.* 100-101:255-263.

In some embodiments of the therapeutic methods disclosed herein, administering an exosomal composition of the presently disclosed subject matter reduces an amount of an inflammatory cytokine in a subject. In some embodiments, the inflammatory cytokine can be interleukin-1β (IL-1β), tumor necrosis factor-alpha (TNF-α), or interleukin-6 (IL-6).

Various methods known to those skilled in the art can be used to determine a reduction in the amount of inflammatory cytokines in a subject. For example, in certain embodiments, the amounts of expression of an inflammatory cytokine in a subject can be determined by probing for mRNA of the gene encoding the inflammatory cytokine in a biological sample obtained from the subject (e.g., a tissue sample, a urine sample, a saliva sample, a blood sample, a serum sample, a plasma sample, or sub-fractions thereof) using any RNA identification assay known to those skilled in the art. Briefly, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, CA). Because the probes to which the nucleic acid molecules of the sample are bound are known, the molecules in the sample can be identified. In this regard, DNA probes for one or more of the mRNAs encoded by the inflammatory genes can be immobilized on a substrate and provided for use in practicing a method in accordance with the presently disclosed subject matter.

With further regard to determining levels of inflammatory cytokines in samples, mass spectrometry and/or immunoassay devices and methods can also be used to measure the inflammatory cytokines in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the antibody to the inflammatory molecule can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the inflammatory molecules is also contemplated by the present invention. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

Mass spectrometry (MS) analysis can be used, either alone or in combination with other methods (e.g., immunoassays), to determine the presence and/or quantity of an inflammatory molecule in a subject. Exemplary MS analyses that can be used in accordance with the present invention include, but are not limited to: liquid chromatography-mass spectrometry (LC-MS); matrix-assisted laser desorption/ionization time-of-flight MS analysis (MALDI-TOF-MS), such as for example direct-spot MALDI-TOF or liquid chromatography MALDI-TOF mass spectrometry analysis; electrospray ionization MS (ESI-MS), such as for example liquid chromatography (LC) ESI-MS; and surface enhanced laser desorption/ionization time-of-flight mass spectrometry analysis (SELDI-TOF-MS). Each of these types of MS analysis can be accomplished using commercially-available spectrometers, such as, for example, triple quadropole mass spectrometers. Methods for utilizing MS analysis to detect the presence and quantity of peptides, such as inflammatory cytokines, in biological samples are known in the art. See, e.g., U.S. Pat. Nos. 6,925,389; 6,989,100; and 6,890,763 for further guidance, each of which are incorporated herein by this reference.

With still further regard to the various therapeutic methods described herein, although certain embodiments of the methods disclosed herein only call for a qualitative assessment (e.g., the presence or absence of the expression of an inflammatory cytokine in a subject), other embodiments of the methods call for a quantitative assessment (e.g., an amount of increase in the level of an inflammatory cytokine in a subject). Such quantitative assessments can be made, for example, using one of the above mentioned methods, as will be understood by those skilled in the art.

The skilled artisan will also understand that measuring a reduction in the amount of a certain feature (e.g., cytokine levels) or an improvement in a certain feature (e.g., inflammation) in a subject is a statistical analysis. For example, a reduction in an amount of inflammatory cytokines in a subject can be compared to control level of inflammatory cytokines, and an amount of inflammatory cytokines of less than or equal to the control level can be indicative of a reduction in the amount of inflammatory cytokines, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Preferred confidence intervals of the present subject matter are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Further provided, in some embodiments, are methods for treating a cancer. In some embodiments, a method for treating a cancer is provided that comprises administering to a subject in need thereof an effective amount of an exosomal composition of the presently disclosed subject matter (i.e., where an exosome encapsulates a therapeutic agent). In some embodiments, the therapeutic agent encapsulated within the exosome and used to treat the cancer is selected from a phytochemical agent, a chemotherapeutic agent, and a Stat3 inhibitor as such agents have been found to be particularly useful in the treatment of cancer. As used herein, the term "cancer" refers to all types of cancer or neoplasm or malignant tumors found in animals, including leukemias, carcinomas, melanoma, and sarcomas.

By "leukemia" is meant broadly progressive, malignant diseases of the blood-forming organs and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

The term "carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "sarcoma" generally refers to a tumor which is made up of a substance like the embryonic connective tissue and is generally composed of closely packed cells embedded in a fibrillar or homogeneous substance. Sarcomas include, for example, chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer. In some embodiments, the cancer is selected from the group consisting of skin cancer, head and neck cancer, colon cancer, breast cancer, brain cancer, and lung cancer.

In some particular embodiments, the cancer is a brain cancer such as, in some embodiments, a glioma. It has been discovered that administering an exosomal composition of the presently disclosed subject matter intranasally to a subject results in the preferential targeting of microglia cells by the exosomal compositions. Microglia cells are known to play a role in many brain diseases and, more specifically, have been implicated in the progression of brain tumor growth and autoimmune diseases. The administration of a exosomal composition of the presently disclosed subject matter, however, results in a significant decrease in the number of microglia cells in the brains of a subject and a concomitant reduction in brain tumor growth. In some embodiments of the methods of treating a cancer disclosed herein, the exosome is administered to the subject by an intranasal, oral, or intratumoral route of administration to thereby treat the cancer. In some embodiments, the exosome specifically binds to a cancerous cell or tissue to thereby precisely deliver the therapeutic agent to the affected cell or tissue of the subject.

As used herein, the term "subject" includes both human and animal subjects. Thus, veterinary therapeutic uses are provided in accordance with the presently disclosed subject matter. As such, the presently disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently disclosed subject matter is further illustrated by the following specific but non-limiting examples. Some of the following examples are prophetic, notwithstanding the numerical values, results and/or data referred to and contained in the examples. The following examples may also include compilations of data that are representative of data gathered at various times during the course of development and experimentation related to the present invention.

EXAMPLES

Materials and Methods for Examples 1-4

MICE. 7- to 10-week female C57BL/6j mice (The Jackson Laboratory, Bar Harbor, ME) were used. All animal studies were conducted within the guidelines established by an Institutional Animal Care and Use Committee.

CHEMICALS AND REAGENTS. Curcumin and lipopolysaccharide (LPS) were purchased from Sigma-Aldrich Co.

CELL CULTURE. An EL-4 mouse lymphoma cell line and RAW 264.7 murine macrophage cell line were utilized and were maintained in vitro at 37° C. in a humidified 5% $CO_2$ atmosphere in air with complete RPMI1640 and DMEM medium supplemented with 10% fetal bovine serum (FBS). The FBS that was used in cell cultures to isolate exosomes was exosome-depleted by differential centrifugation using a method described previously (22).

PREPARATION OF EXOSOMES. The cell culture supernatants were collected and used for exosome purification by differential centrifugation using a previously described method (22). Purity and integrity of sucrose gradient isolated exosomes were analyzed using a Hitachi H7000 electron microscope as previously described (23). The concentration of exosomes was determined by analyzing protein concentration using a standard protein quantitation assay kit with bovine serum albumin (BSA) as a standard. The protein expression of exosomes was determined by western blotting analysis as described previously (23).

PREPARATION OF EXOSOMAL CURCUMIN. Exosomal curcumin was prepared by mixing curcumin with EL4 exosomes in PBS. After incubation at 22° C. for 5 min, the mixture was subjected to sucrose gradient (8%, 30%, 45% and 60%, respectively) centrifugation for 1.5 h at 36,000 rpm. The exosomal curcumin, distinguished as a yellowish band in the sucrose gradient between 45% and 60%, was subsequently collected, washed and dissolved with PBS. The concentration of exosomes and curcumin within the complex was then determined as described below. Based on the morphology and protein expression, the vesicles were further determined to be exosomes (23).

ANALYSIS OF CURCUMIN CONCENTRATION IN VITRO AND IN VIVO. The concentration of curcumin in samples in vitro was determined using a Nanodrop 1000 spectrophotometer (NanoDrop product, Wilmington, DE) at 420 nm. Briefly, to evaluate the concentration of curcumin, a standard curve of curcumin was plotted first. A stock solution of curcumin was diluted to a range of 5 to 50 µM. A standard calibration curve was obtained by plotting the concentration of standard curcumin versus fluorescent absorbance at 420 nm ($OD_{420}$). The curcumin quantity in cell culture supernatant or PBS was calculated based on the $OD_{420}$ with respect to the concentration of curcumin in the diluted standards.

High-performance liquid chromatography (HPLC) analysis was then adapted to determine the concentration of curcumin as described previously (24). To determine the concentration of curcumin in plasma, a standard curve of curcumin was plotted first. Briefly, a stock solution of curcumin (0.5 mg/ml) in acetonitrile was diluted to a range of 0.1 to 5 µg/ml with acetonitrile, and then 10 µl of diluted curcumin were added to 90 µl of plasma isolated from naïve C57BL/6j mice (a range of 1-500 ng/ml). The mixture was added to an equal volume of emodin (0.15 µg/ml, Sigma, St. Louis, MO) and vortexed for 5 min at 22° C. After centrifugation at 2500×g for 15 minutes to remove precipitated plasma proteins, 50 µl of each of the working solutions containing 1 to 500 ng/ml of curcumin was then analyzed by HPLC. The chromatographic separation was performed on a C18 column (aappTec, 5 µm, 250×4.6 mm) with the mobile phase composed of acetonitrile-5% acetic acid (75:25, v/v) at a flow rate of 1.0 ml/min. The wavelength of detection was at 420 nm. A standard calibration curve was obtained by plotting the concentration of standard curcumin versus absorbance units (AU).

To determine the concentration of curcumin in the samples, plasma samples collected from mice treated with exosomal curcumin or free curcumin were precipitated with emodin to remove proteins and analyzed using an identical method as described above. The concentration was calculated using the absorbance units with respect to the concentration of curcumin in the standard curve.

FACS ANALYSIS. For cell surface marker staining, isolated cells were blocked at 4° C. for 5 min with 10 µg/ml mouse Fc block (BD Biosciences, San Jose, CA) and then reacted with various fluorochrome-labeled antibodies including appropriate isotype controls for 30 min at 4° C. After washing twice, cells were fixed and analyzed using a FACSCalibur flow cytometer (Becton Dickinson Biosciences, San Jose, CA). Data were analyzed using FlowJo software (Tree Star, Inc., Ashland, OR). The following antibodies were used for immunostaining: FITC-AnnexinV (Invitrogen, Carlsbad, CA), APC anti-mouse CD11b and PE anti-mouse Gr-1 (eBiosciences, San Diego, CA).

IN VITRO STABILITY ASSAYS. To determine the stability of free curcumin and exosomal curcumin in PBS (pH 7.4), curcumin and exosomal curcumin were added to 2 ml PBS to achieve a final concentration of 30 µM and incubated in the dark in a 37° C. water bath. At different time points, 100 µL of each sample were taken to determine the concentration of curcumin. The concentrations of curcumin or exosomal curcumin at the beginning were considered as 1.00. The fold reduction of the concentration at each time was determined by comparison to the beginning value. The experiments were repeated three times for each time point (n=3).

IN VIVO BIOAVAILABILITY ASSAYS. To determine the bioavailability of free curcumin and exosomal curcumin in vivo, two groups (5 per group) of C57BL/6j mice were intra-peritoneally (IP) injected or administrated orally with 100 mg curcumin or exosomal curcumin/kg body weight. At 0.5 hr, 1 hr and 2 hr, blood samples were taken through eye bleeding and the concentration of curcumin in the plasma was determined by HPLC as described above. Naïve mice without treatment were used as blank controls.

IN VITRO PRO-INFLAMMATORY CYTOKINE INDUCTION ASSAYS. RAW cells were plated on 24-well plates and incubated overnight. The cells were treated with curcumin or exosomal curcumin at a concentration of 20 µM for 1 h and then stimulated with lipopolysaccharide (LPS; 50 ng/ml) for an additional 6 hr. RAW 264.7 cells treated with PBS or exosomes served as controls. Tumor necrosis factor-alpha (TNF-α□□□ and Interleukin-6 (IL-6) levels in the cell culture supernatant were measured using a standard ELISA (eBiosciences, San Diego, CA).

LPS MOUSE SEPTIC SHOCK MODEL. Curcumin or exosomal curcumin (4 mg/kg of body weight) was IP injected into C57BL/6j mice together with LPS (18.5 mg/kg, Sigma, St. Louis, MO). EL-4 exosomes equal to the amount in exosomal curcumin and PBS were used as controls. Mouse mortality was monitored over a period of 4 days. The sera were collected 16 hr after LPS injection and used to determine IL-6 and TNF-α levels using ELISAs as before. At day 1 after LPS challenge, 3 mice from each treated group were sacrificed and the leukocytes in the lungs were isolated using a method described previously (21). The percentage of CD11b$^+$Gr-1$^+$ cells in the lung was determined by FACS analysis.

ISOLATION OF Gr1$^+$ CELLS FROM MOUSE BONE MARROW CELLS. Mouse bone marrow cells were isolated as described previously (22). The isolated bone marrow cells were re-suspended to a concentration of 1×10$^8$ cells/ml using RPMI 1640 medium supplemented with 10% FBS. A Gr1-PE conjugated antibody (3 µg/ml), following a mouse FcR blocking specific antibody (5 µl/ml), was added, mixed thoroughly and incubated at 4° C. for 15 min. After centrifugation at 1500 rpm for 5 min, cells were re-suspended in fresh medium to a concentration of 1×10$^8$ cells/ml. EasySep® PE selection cocktail (25 µl/ml, StemCell Technologies, Vancouver, British Columbia) was added to the cells and incubated at 4° C. for 15 min. Afterwards, EasySep® magnetic nanoparticles (25 µl/ml) were added and incubated at 4° C. for another 15 min. Culture medium was added to a final volume of 2.5 ml and the cells mixed by gentle pipetting of the mixture 2-3 times. The uncapped polystyrene tube was placed into the EasySep® magnet and set aside for 5 min. The supernatant containing unbound cells was removed leaving the magnetically bound Gr1$^+$ cells. A second round of magnetic separation was done on the supernatant. Positively selected (magnetically bound) cells were collected from the tubes, counted and cultured in RPMI 1640 supplemented with MCSF (20 ng/ml) for curcumin uptake and apoptosis assays.

STATISTICAL ANALYSIS. Statistical differences between groups were determined by ANOVA with multiple comparisons using Fisher's post hoc analysis. The Student's t test was used for comparisons when only two parameters were evaluated. $P<0.05$ was considered significant.

Example 1—Encapsulation of Curcumin into Exosomes

Figure 1B:
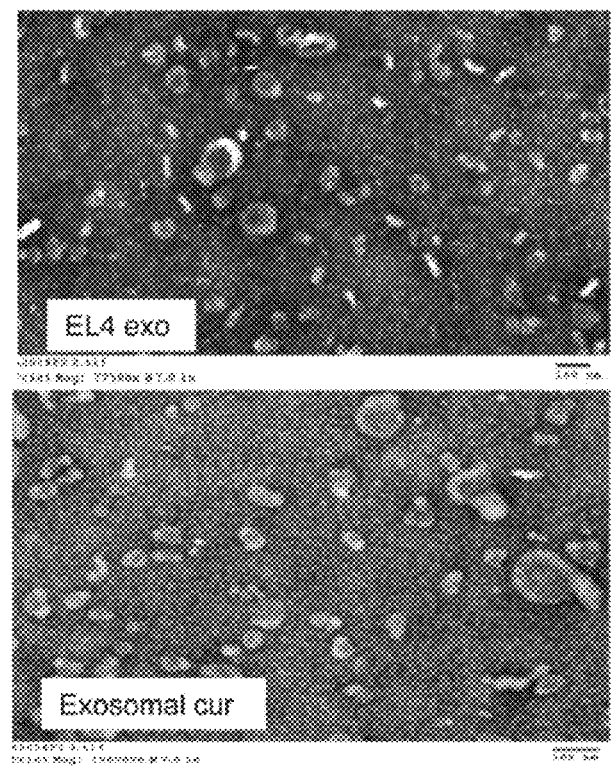
FIG. 1B includes electron microscopy images showing the morphology and size of exosomes isolated from an EL4 mouse lymphoma cell line ("EL4 exo"; upper image) as compared to EL4 exosomes that encapsulate curcumin ("Exosomal cur"; lower image)
Figure 1C:
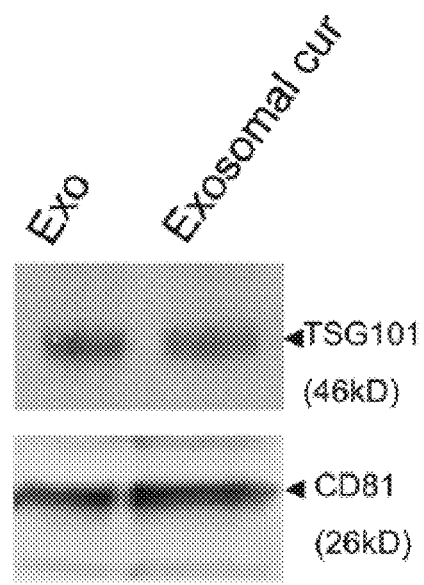
FIG. 1C includes images of a western blot analysis of EL4 exosomes and exosomal curcumin protein expression, where the upper image shows the presence of the exosomal protein TSG101 and the lower image shows the presence of the exosomal protein CD81.

Exosomes are 30-100 nm nanoparticles (FIG. 1B) secreted by cells into the extracellular environment. To determine if nanoparticle exosomes could be used as a carrier to entrap curcumin, curcumin was mixed with EL4-derived exosomes at 22° C., and then subjected to sucrose gradient centrifugation. A yellowish band (FIG. 1A, right) appeared between the 45% and 60% sucrose gradients, and a weak band appeared between the 30% and 45% gradients (original exosomes, FIG. 1A, left). The yellowish band was collected, washed and dissolved in PBS. This fraction was designated exosomal curcumin. The morphology and the size of exosomal curcumin were similar to the original exosomes (FIG. 1B). Exosomal protein markers, such as TSG101 and CD81 (FIG. 1C) were identified in the exosomal curcumin. The binding affinity was calculated to be approximately 2.9 g curcumin to 1 g exosomes. Exosomes isolated from other types of cell lines, including MDA-MB231 (human adenocarcinoma), 4T-1 (murine breast tumor cell line) and primary mouse embryonic fibroblasts, were also observed to have also have similar efficiency in terms of binding curcumin.

Figure 2A:
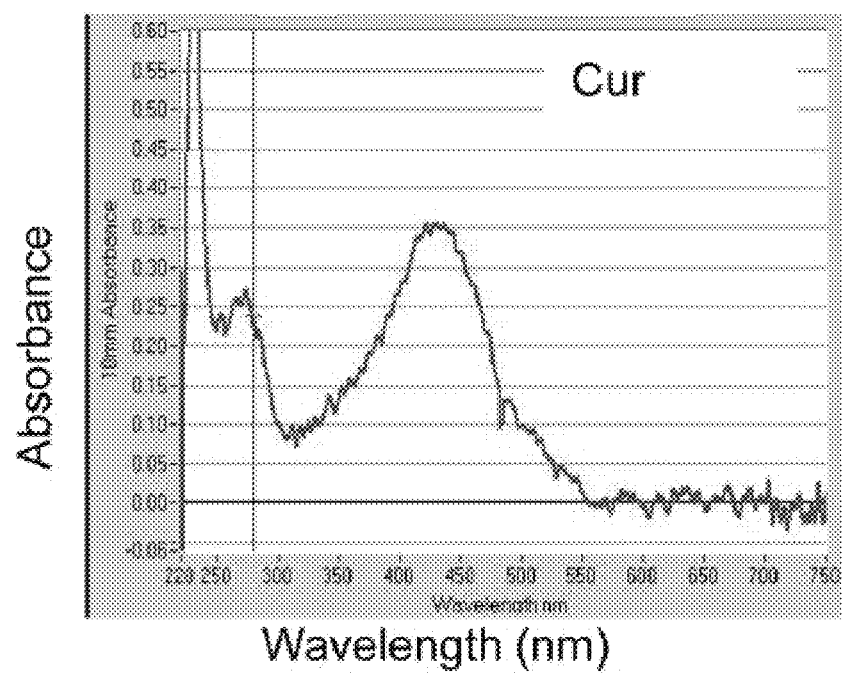
FIG. 2A is a spectrograph used to measure the concentration of free curcumin in phosphate-buffered saline (PBS) in control samples.
Figure 2B:
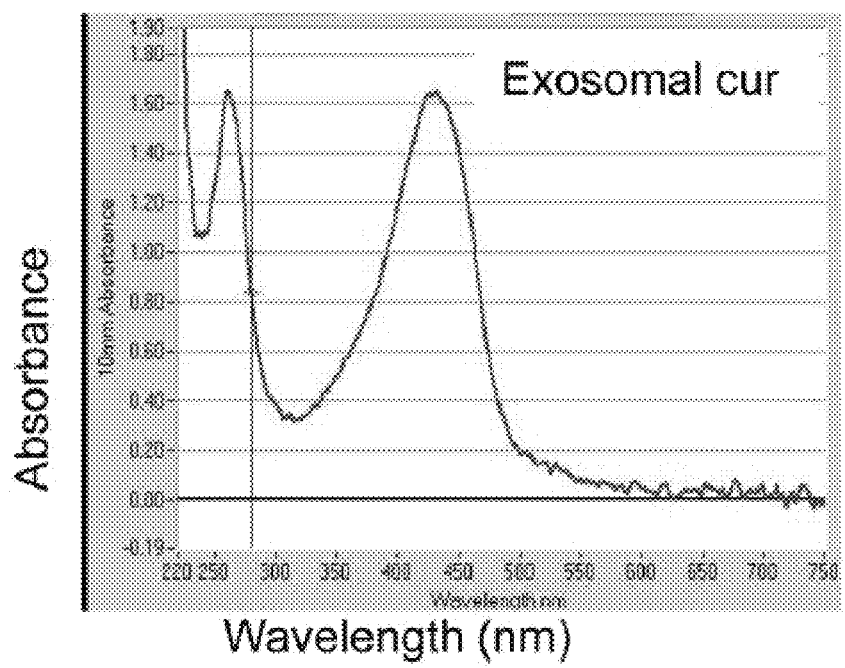
FIG. 2B is a spectrograph used to measure the concentration of curcumin encapsulated in EL4 exosomes.

Example 2—Encapsulation of Curcumin into Exosomes Increases Curcumin's Solubility, Stability and Bioavailability Curcumin is a hydrophobic polyphenol compound that is insoluble in aqueous solution. To determine if the binding of curcumin to exosomes increased the solubility of curcumin, an identical amount of curcumin was mixed in an equal volume of PBS or exosomes in PBS, and the mixtures were placed on ice for 30 min. To estimate curcumin solubility, the concentration of curcumin in the supernatant was determined using a Nanodrop 1000 spectrophotometer. The curcumin concentration in the mixture of curcumin and exosomes was appropriately 5 fold higher than curcumin alone (FIGS. 2A-2B). Thus, the solubility of exosomal curcumin is higher than free curcumin and this is believed to be due to the binding of curcumin to exosomes.

Figure 2C:
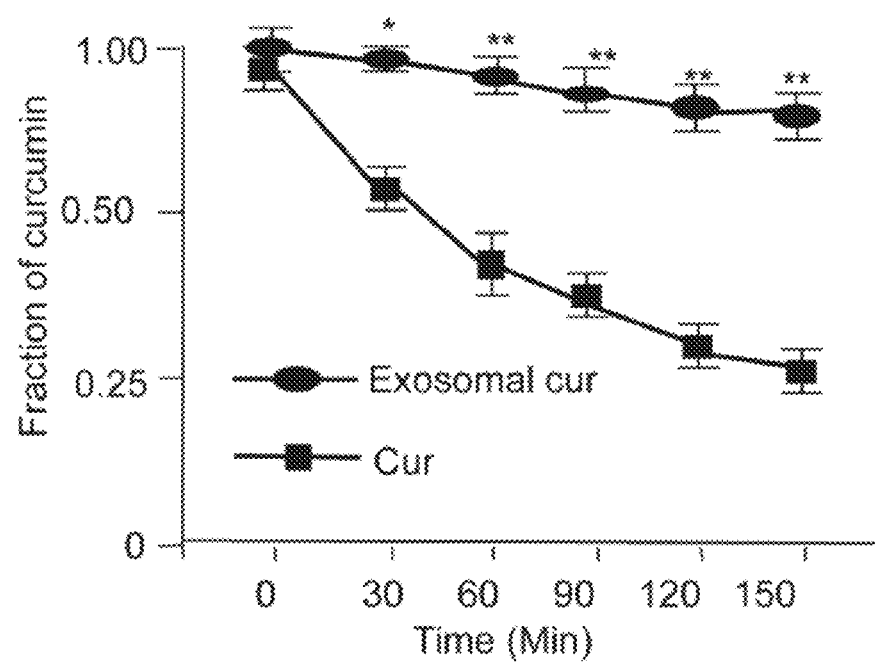
FIG. 2C is a graph showing the degradation of curcumin and exosomal curcumin after the incubation of samples at 37° C., where concentrations of curcumin and exosomal curcumin were measured at 30, 60, 90, 120, and 150 min.

Curcumin is relatively unstable, and this is one of the major barriers for clinical use of curcumin to treat cancer and other inflammation related diseases (15). To determine whether exosomal curcumin is more stable, free curcumin and exosomal curcumin were incubated at 37° C. over a period of 150 min and sampled periodically to determine the concentration of curcumin. After incubation for 150 min at 37° C., it was found that free curcumin in PBS degraded quickly and only 25% remained after 150 min of incubation when compared to the 0 min sample (set as 1.0). Curcumin in exosomal curcumin was protected from degradation with more than 80% remaining after 150 min incubation in PBS (pH 7.4, FIG. 2C).

Figure 3A:
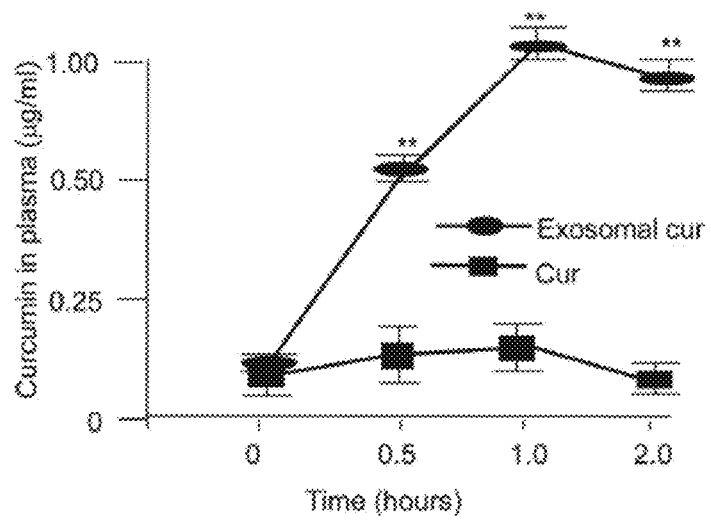
FIG. 3A is a graph showing the concentration of curcumin and exosomal curcumin at various time points in the plasma of mice that were intraperitoneally injected with 100 mg/kg body weight of curcumin or exosomal curcumin.
Figure 3B:
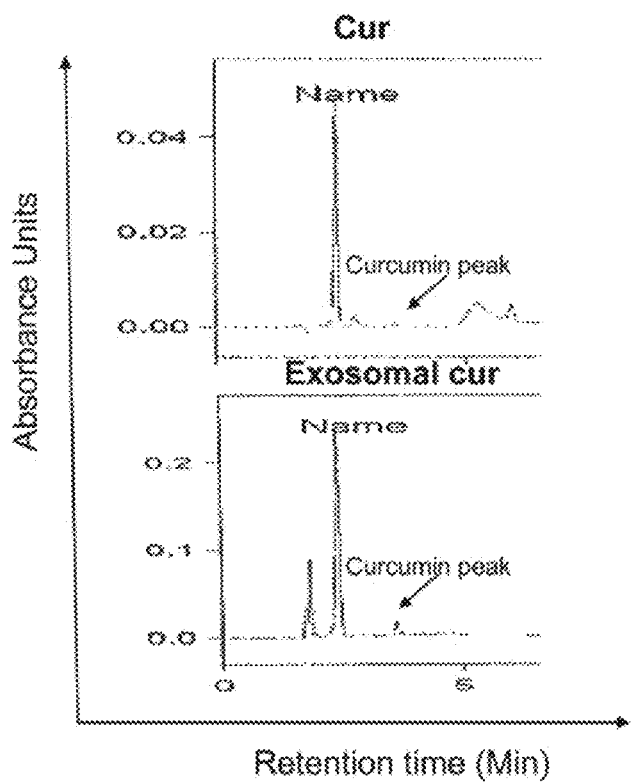
FIG. 3B includes chromatograms from high-performance liquid chromatography experiments that were performed with blood samples of mice, where the samples were taken 30 minutes after intraperitoneally injecting the mice with 100 mg/kg body weight of curcumin or exosomal curcumin.

Another major barrier for clinical use of curcumin is its low systemic bioavailability (15). After administering curcumin orally, curcumin is digested in the stomach. Along with other food, curcumin then passes through the intestinal wall into the enterohepatic circulation, arriving in the liver for detoxification (the first pass effect) and eventually gets into the blood stream. The low bioavailability of curcumin may be due to the rapid first pass effect and the fast intestinal glucuronidation metabolism. Nanoparticles for drug delivery can increase drug bioavailability through accumulating in the reticulo-endothelial system (RES) and achieving enhanced permeability and retention effects (EPR effect) (1). To assess if exosomal curcumin can increase the bioavailability of curcumin, free curcumin and exosomal curcumin (before purification, see Material & Methods for Example 1-4) was administered IP or orally at a dose of 100 mg/kg of body weight. Due to the low bioavailability of curcumin, a high dose of curcumin was used to achieve detectable curcumin in curcumin treated mice. Curcumin in the plasma was then quantified at 0.5, 1, and 2 hr after the administration using an established HPLC method (see, e.g., FIG. 3B). FIG. 3A shows that at 30 min, IP administration of exosomal curcumin led to a 5 to 10 fold higher curcumin accumulated in peripheral blood than that of curcumin alone. At 120 min after IP injection, curcumin in the plasma still remained at a much higher level in the group of mice injected with exosomal curcumin. In contrast, there was no detectable curcumin circulating in the blood of mice treated with curcumin alone. Similar results were obtained when mice were administrated curcumin or exosomal curcumin orally.

Example 3—Anti-Inflammation Activity of Exosomal Curcumin

Figure 4:
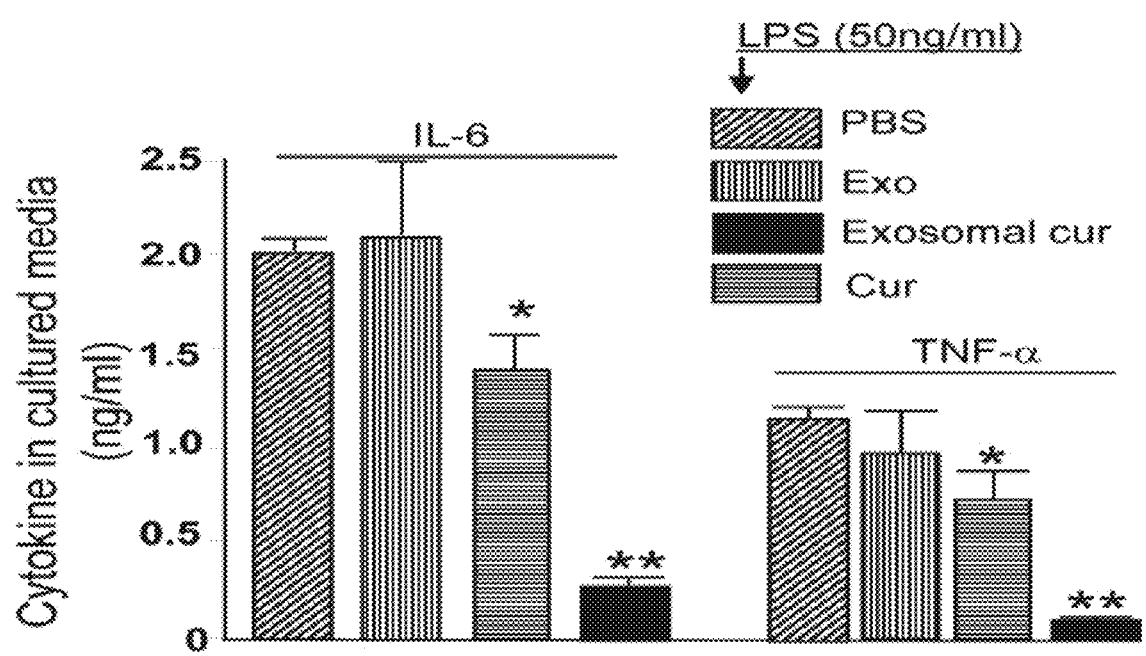
FIG. 4 is a graph showing the amounts of interleukin-6 (IL-6) and tumor necrosis factor-alpha (TNF-α) in cell culture supernatants, where the cells where treated with PBS, EL4 exosomes, exosomal curcumin, or free curcumin.

The foregoing data show that, as a nanoparticle drug carrier, exosomes can increase the solubility and stability of curcumin in vitro, and the bioavailability of curcumin in vivo. In this regard, it was hypothesized that exosomal curcumin can enhance the anti-inflammatory activity of curcumin through accumulating curcumin to a high level in cellular targets. To evaluate the anti-inflammatory activity of exosomal curcumin in vitro, RAW 264.7 cells were treated with curcumin or exosomal curcumin at a concentration of 20 µM for 1 hr. Subsequently treated cells were stimulated with LPS (50 ng/ml) for an additional 6 hr. Cytokine production in the supernatant was measured 6 hr post treatment. As shown in FIG. 4, exosomal curcumin treated macrophages produced significantly less IL-6 and TNF-α in comparison with curcumin treatment alone.

Figure 5A:
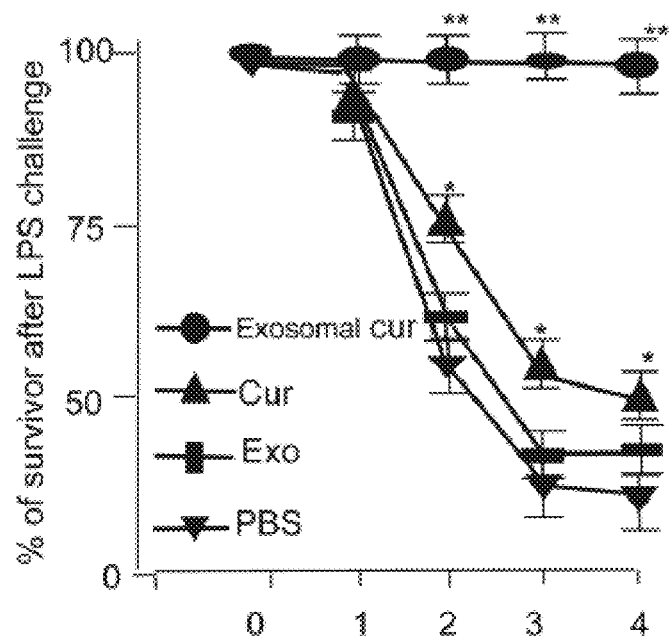
FIG. 5A is a graph showing the percent of surviving mice subsequent to the administration of lipopolysaccharide (LPS) and PBS, EL4 exosomes, exosomal curcumin, or free curcumin.
Figure 5B:
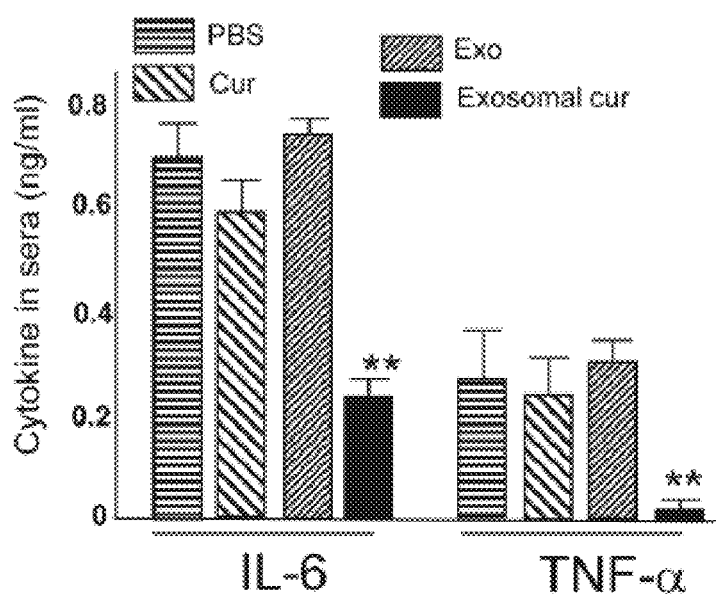
FIG. 5B is a graph showing the serum levels of IL-6 and TNF-α in mice subsequent to the administration of lipopolysaccharide (LPS) and PBS, EL4 exosomes, exosomal curcumin, or free curcumin.

To assess the anti-inflammatory activity of exosomal curcumin in vivo, a LPS induced septic shock model was adapted. Briefly, to monitor mice mortality, a $LD_{50}$ (median lethal dose) of LPS was determined first. LPS (5 mg/ml, Sigma, St. Louis, MO) was then prepared with sterile $H_2O$ and varied amounts of LPS were IP injected into the same batch of commercially supplied C57BL/6j mice. Each group contained 6 mice. The $LD_{50}$ was 18.75 mg of LPS/kg of body weight. C57BL/6j mice were IP injected with LPS (18.75 mg/kg) together with curcumin or exosomal curcumin (4 mg/kg body weight) treatments. There was a significant survival advantage for mice treated with exosomal curcumin as compared to mice treated with an equivalent concentration of free curcumin over a 4-day period (FIG. 5A). Exosomes and PBS injections served as controls. Sixteen hours after IP injection of LPS, the sera levels of IL-6 and TNF-α were similar in mice treated with free curcumin, exosomes, and PBS. However, both cytokines were significantly lower in the exosomal curcumin treated group of mice (FIG. 5B) and this finding correlated with mice mortality.

Example 4—Exosomal Curcumin Decreased $Cd11b^+Gr1^+$ Cells in the Lungs of Mice

Figure 6A:
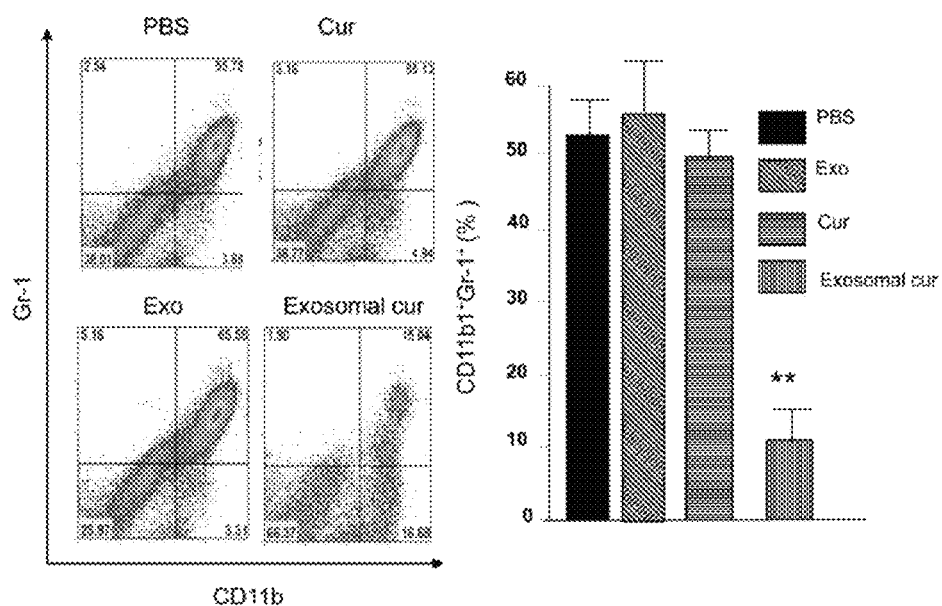
FIG. 6A includes an image and a graph showing the fluorescence activated cell sorter (FACS) analysis of $CD11b^+Gr1^+$ cells in leukocytes that were isolated from the lungs of mice who were administered PBS, EL4 exosomes, exosomal curcumin, or free curcumin.
Figure 6B:
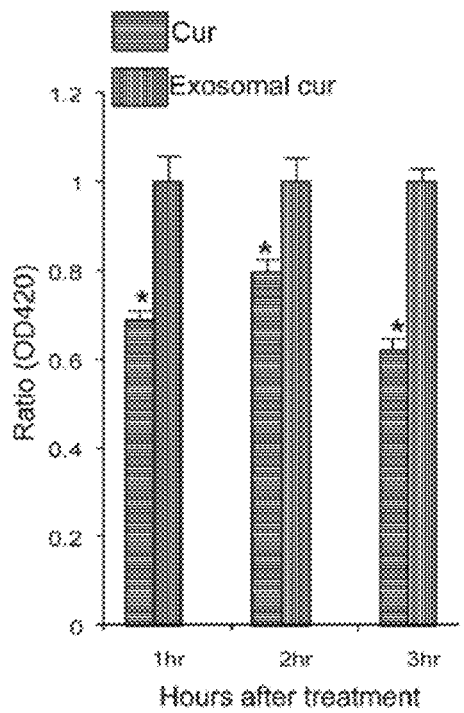
FIG. 6B is a graph showing the cellular curcumin concentration in $Gr1^+$ cells isolated from bone marrow cells and then treated with the same concentration of either free curcumin or exosomal curcumin.
Figure 6C:
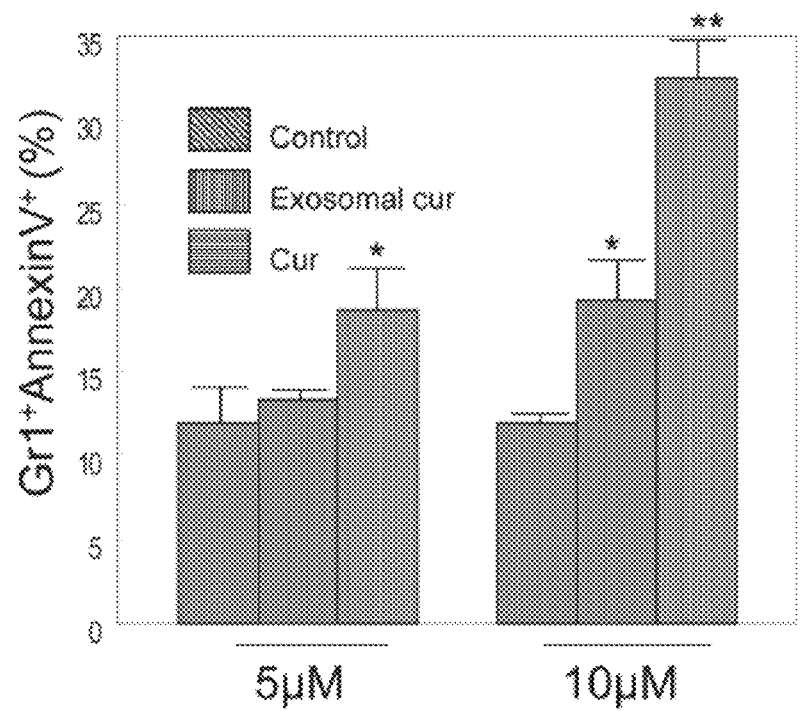
FIG. 6C is a graph depicting the extent of cell death in $Gr1^+$ cells treated with 5 µM or 10 µM of free curcumin or exosomal curcumin, where the cells were treated for 8 hours and then stained with Annexin V-FITC.

One of the features of LPS induced septic shock is a robust increase of the number of $CD11b^+Gr-1^+$ cells that are sequestered in the lungs leading to acute lung inflammation (26, 27). In LPS treated mice, there were significantly fewer $CD11b^+Gr-1^+$ cells in the lungs, but not in other organs of the mice treated with exosomal curcumin when compared to mice treated with curcumin, exosomes or PBS (FIG. 6A). It has been reported previously that tumor exosomes are taken up by $CD11b^+Gr-1^+$ cells circulating in the peripheral blood (25, 28). To evaluate whether exosomal curcumin can take advantage of this property, $Gr1^+$ cells were isolated from bone marrow cells and co-cultured with curcumin or exosomal curcumin at the same concentration. At 1, 2, and 3 hours, cellular curcumin concentration was significantly higher in exosomal curcumin treated cells than free curcumin treated cells (FIG. 6B); an increase in curcumin did not occur in cells treated with an equivalent amount of exosomes and curcumin together. Interestingly, curcumin induces $Gr1^+$ cell apoptosis when $Gr1^+$ cells are treated with 5 µM and 10 µM curcumin, and exosomal curcumin can significantly enhance this induction as determined by FACS analysis (FIG. 6C). $Gr1^+$ cells treated with an equivalent amount of exosomes and curcumin had a similar apoptosis induction as curcumin treatment alone, and $Gr1^+$ cells treated with exosomes alone had a similar apoptosis percentage as the controls. Without wishing to be bound by any particular theory, it was thought that the increase in curcumin uptake by $Gr1^+$ cells with an increased cell apoptosis caused by exosomal curcumin treatment can be the reason fewer $CD11b^+Gr1^+$ cells were found in the lungs and the mice were protected from LPS induced septic death.

Discussion of Examples 1-4

The foregoing examples indicate that nanoparticle exosomes can carry and deliver curcumin in a manner that enhances the anti-inflammatory activity of curcumin through: 1) increasing the solubility, stability and bioavailability of curcumin, and 2) enhancing and increasing the delivery of curcumin to activated monocytes. The approach described herein above also leads to the protection of mice from LPS induced septic shock. Furthermore, the above data demonstrates that exosomes target not only $CD11b^+Gr-1^+$ cells in peripheral blood but also enhance and increase the delivery of exosomal curcumin to CD11b Gr-17 cells, thus inducing more cell death. $CD11b^+Gr-1^+$ cells are one of the major cellular populations associated with disease pathogenesis. Accumulation of $CD11b^+Gr-1^+$ cells can suppress host immune responses and interrupt immunosurveillance, which provides an explanation as to why long-term inflammation promotes tumor progression. Exosome directed curcumin targeting to $CD11b^+Gr-1^+$ cells provides a means to treat inflammatory disorders and cancers.

As noted, the foregoing data indicate that encapsulation of curcumin into exosomes can increase the solubility, stability and bioavailability of curcumin. Exosomes, which contain a lipid bilayer, can load curcumin through physical entrapment. Through the hydrophobic interaction between the hydrophobic tails and hydrophobic drug, curcumin can be self-assembled into the lipid bilayer of exosomes and this may protect curcumin from degradation. Nanoparticles are distributed to organs in a size dependent selective manner (30). Sizes less than 5 nm nanoparticles are preferentially distributed to kidney and liver. Larger sized exosomes likely stay in the vasculature for an extended time. When formulated with curcumin, exosomes increase curcumin water solubility and stability, and result in better delivery to the blood stream and increased bioavailability.

Exosome-based drug delivery renders hydrophobic drugs, like curcumin, capable of being dispersed in aqueous environments, thus circumventing the pitfalls of poor stability and bioavailability. The foregoing results indicate that this strategy is applicable for treating monocyte-mediated acute inflammation-related diseases and can be useful in preventing chronic inflammation triggered diseases, such as obesity, and cancers. Finally, unlike other non-host delivery vehicles, host-derived exosomes have an advantage as a potential delivery vehicle because they do not induce an immune response with subsequent side effects.

Materials and Methods for Examples 5-8

REAGENTS. Curcumin, JSI-124 (cucurbitacin I) and LPS were purchased from Sigma-Aldrich (St Louis, MO) and dissolved in DMSO as stock solutions. A rabbit anti-Iba1 antibody that specifically recognizes microglia cells and macrophages was purchased from Wako Chemicals (Richmond, VA). Antibodies directly against total and phospho-Stat3 were purchased from Cell Signaling Technology Inc. (Danvers, MA). The following fluorescent dye-conjugated Abs were obtained from e-Bioscience (San Diego, CA): anti-CD11b, Anti-CD45.2, and anti-IL-1β.

CELL LINES. The mouse ($H-2^b$) glioma cell line GL26 stably expressing the luciferase gene (GL26-Luc) and the BV2 microglia cell line were provided by Dr. Behnam Badie (Beckman Research Institute of City of Hope, Los Angeles), and maintained in RPMI 1640 media supplemented with 10% heat-inactivated FBS in a humidified $CO_2$ incubator at 37° C. Cell lines including 3T3L1, 4T1, CT26, A20, and EL4 were purchased from the American Type Culture Collection (ATCC; Manassas, VA) and cultured according to the protocols provided by the ATCC.

PREPARATION OF EXOSOMES AND EXOSOMAL CURCUMIN (Exo-cur) AND) JSI-124 (Exo-JSI-124). All exosomes used in this study were prepared according to the protocols described herein above. Microparticles were prepared from supernatants of tumor cells grown to confluence (48 h). The supernatants were sequentially centrifuged at 500×g for 10 minutes and then at 1200×g for 30 minutes. Microparticles were then pelleted at 10,000×g for 1 hour and washed once in PBS. The concentration of exosomes and microparticles was determined by analyzing protein concentration using the Bio-Rad protein quantitation assay kit (Bio-Rad, Hercules, CA) with bovine serum albumin serving as a standard. Both Exo-cur and Exo-JSI-124 were prepared by mixing curcumin or JSI-124 with EL-4 exosomes in PBS. After incubation at 22° C. for 5 minutes, the mixture was subjected to sucrose gradient (8, 30, 45, and 60%, respectively) centrifugation for 1.5 hours at 36,000 rpm. Exo-cur or Exo-JSI-124 was subsequently collected, washed, and resuspended in PBS. The concentration of curcumin or JSI-124 in the complex was determined by HPLC analysis as also described herein above.

ANIMALS. C57BL/6j mice ($H-2^b$) were purchased from the Jackson Laboratory. Animals were housed in the animal facility at the University of Louisville per an Institutional Care and Use Committee-approved protocol.

INTRANASAL DELIVERY OF EXOSOMES, EXO-CUR AND EXO-JSI-124 IN MICE. For intranasal administration of exosomes or exosome encapsulated drugs, C57BL/6j mice were anesthetized by inhalation with 2%-2.5% isoflurane and placed in a supine position in an anesthesia chamber. PBS (2 µl) containing exosomes (300 pmol/2 µl), or Exo-cur or Exo-JSI-124 were administered intranasally as drops with a small pipette every 2 min into alternating sides of the nasal cavity for a total of 10 min. A total volume of 10 µl was delivered into the nasal cavity.

To determine the bioavailability of free curcumin and exosomal curcumin in vivo, two groups (five per group) of C57BL/6j mice were administrated 1.5 nmol curcumin or Exo-cur intranasally. At 0, 3, 6, 12, and 24 hours, the olfactory bulb was removed and curcumin was extracted from the tissue as described herein above. The concentration of curcumin in the extracts was again determined by HPLC methodology. The extracts from olfactory bulb of naive mice without treatment either mixed with a known amount of curcumin or PBS were used as positive and negative controls, respectively.

To monitor the trafficking of exosomes administered intranasally, exosomes were first labeled using an Odyssey fluorescent dye IRDye800 kit (LI-COR Biosciences, Lincoln, NE) and a previously described method (82). To localize EL-4 exosomes in brain tissue, the IRDye 800CW-labeled EL-4 exosomes (10 µg/10 µl in PBS) were 1 administrated intranasally to C57BL/6j mice as described above. The mice were imaged over a 48-hour period using a prototype LI-COR imager (LI-COR Biosciences). For controls, mice (five per group) received nonlabeled EL-4 exosomes in PBS or free IRDye800 dye at the same concentration for IRDye800 dye labeled exosomes.

IDENTIFYING THE BRAIN CELLS TARGETED BY EXOSOMES ADMINISTRATED INTRANASALLY. Mice were administered intranasally PHK26 fluorescent dye labeled exosomes (10 µg/mouse in 10 µl PBS) using the method described above. After intranasal administration, mice were transcardially perfused with PBS followed by a 4% paraformaldehyde (PFA) solution at pH 7.4. Brain tissue was postfixed overnight in 4% PFA and then cryopreserved in phosphate-buffered 30% sucrose. Brains were embedded in Tissue-Tek (OCT compound, Sakura, USA) and kept at −20° C. overnight. Brain tissue sections were cut with a Cryostat (30 µm thick) and the tissue sections stored at −20° C. Immunofluorescent staining of microglia cells with rabbit anti-Iba1 antibody was carried out according to previously described procedures (83). Tissues evaluated for the presence of Iba1 positive staining were assessed using a Zeiss LSM 510 confocal microscope equipped with a digital image analysis system (Pixera, San Diego, CA).

BRAIN TUMOR-BEARING MICE MODEL. $5 \times 10^4$ GL26-Luc cells per mouse were intracranially injected using a method described previously (84). In brief, using a Hamilton syringe (Hamilton Company, Reno, NV), $5 \times 10^4$ GL26-Luc cells in 2 µl PBS were stereotactically injected through an entry site at the bregma of anesthetized mice. Typically this procedure results in a 100% tumor take and a median survival time of approximately 22 days after tumor implantation. Tumor-bearing mice were treated intranasally for 12 consecutive days with daily doses of 12.5 pmol Exo-JSI-124, or JSI-124-(12.5 µmol) or Exo-control in PBS or PBS-control. Treatment was initiated on day 3 after tumor cells were injected intracranially. The investigators treating the animals were fully blinded with regard to treatment. All mice were monitored every day and euthanized when they exhibited neurological symptoms indicative of impending death.

Monitoring the growth of injected tumor cells was accomplished by quantifiying luciferase activity over a 15-day period post-tumor cell injection using a previously described method (85) with minor modifications. In brief, prior to the imaging session, the mice received an intraperitoneal (IP) injection of D-luciferine, a luciferase substrate (150 mg/kg, Xenogen, Alameda, CA) dissolved in PBS. The mice were then anesthetized with 2% isoflurane in 100% oxygen at a flow rate of 2 mL/min. Images were collected using a high-sensitivity CCD camera with wavelengths ranging from 300 to 600 nm with an exposure time for imaging of 2 min. Regions of interest were analyzed for luciferase signals using Living Image 2.50 software (Xenogen) and was reported in units of relative photon counts per second. The total photon count per minute (photons per minute) was calculated (5 animals) using Living Image software. The effects of treatment versus non-treatment on brain tumor bearing mice was determined by dividing the number of photons collected for treated mice by the number of photons collected for untreated mice at different imaging time points. Results were represented as pseudocolor images indicating light intensity (red and yellow being the most intense) that were superimposed over grayscale reference photographs.

LPS INDUCED BRAIN INFLAMMATION. Bacterial lipopolysaccharide (LPS) (2.5 mg/kg, Sigma-Aldrich) was injected IP into C57BL/6j mice. Immediately after LPS injection, mice were administrated intranasally curcumin, exo-cur (1.5 nmol in 10 µl PBS), or EL-4 exosomes equal to the amount in exosomal curcumin. EL-4 exosomes and PBS served as controls. Two h after the treatments five mice from each group of mice (10 mice per group) were sacrificed and the skulls of the mice were removed, the exposed brains were photographed, and the brains were subsequently fixed for analysis of apoptosis induction using a method described previously (86, 87). Four hours after the treatments, the remaining mice (5 mice per group) in each group were sacrificed and brain leukocytes were isolated. The percentage of activated microglia cells and apoptotic cells was determined by fluorescence-activated cell sorting (FACS) analysis of CD45.2$^+$IL-1β$^+$ cells and PI$^+$ annexinV positive staining cells, respectively. Apoptosis in the brain was also evaluated by fluorescence using an in situ cell death detection kit (Roche) according to manufacturer's protocol. The expression of IL-1β in CD45.2$^+$IL-1β$^+$ cells was quantified by real-time PCR (88).

EXPERIMENTAL AUTOIMMUNE ENCEPHALITIS (EAE) INDUCTION AND TREATMENT WITH EXO-CUR IN VIVO. EAE was induced in six-week-old female C57BL/6 mice using a procedure described previously (67). Briefly, mice were primed subcutaneously in the flanks with 150 μg of Myelin Oligodendrocyte Glycoprotein (MOG) 35-55 peptide (Biosynthesis, Lewisville, TX) per animal. The peptide was emulsified in complete Freund's adjuvant (CFA) containing 1 mg/ml of *Mycobacterium tuberculosis* H37RA (Difco, Detroit, MI). Two days later the mice were injected IP with 500 ng of Pertussis toxin (Alexis Corp., San Diego, CA) in 100 μl of PBS. Mice (n=10) were treated intranasally with daily doses of 1.5 nmoles of Exo-cur, or with Cur- or Exo-controls in PBS or PBS-control for 26 consecutive days. Treatment was initiated on day 4 after mice were primed with MOG35-55 peptide. The mice were scored as follows: 0, no detectable signs of EAE; 1, complete limp tail; 2, limp tail and hindlimb weakness; 3, severe hindlimb weakness; 4, complete bilateral hindlimb paralysis; 5, total paralysis of both forelimbs and hindlimbs or death.

ISOLATION OF BRAIN LEUKOCYTES. Brain leukocytes were isolated using a method described previously (89). In brief, mice were sacrificed by $CO_2$ asphyxia, then perfused through the left cardiac ventricle with PBS. Brains were minced mechanically and cells from each brain were resuspended in 70% Percoll (Sigma-Aldrich, St. Louis, MO), overlayed with 37 and 30% Percoll, and centrifuged for 20 min at 500×g at 22° C. Enriched brain leukocyte populations were recovered at the 70-37% Percoll interface. Quantification of subset populations present in the isolated cells was determined by antibody staining followed by FACS analysis (89) or western blot analysis of cell specific proteins.

For FACS analysis of cell apoptosis, an annexin-V fluorescein isothiocyanate/PI double-stain assay was performed according to the manufacturer's protocol (BioVision, Mountain View, CA). Briefly, leukocytes isolated from brain tissue were washed and resuspended in 500 μl of binding buffer containing 5 μl of annexin-V fluorescein isothiocyanate and 5 μl of PI. The cells were incubated for 5 minutes in the dark at 22° C. Analysis was done immediately using a flow cytometer.

WESTERN BLOT. Western blots were done as previously described (90). In brief, cells were lysed and proteins of lysed cells were separated on 10% polyacrylamide gels using SDS-PAGE. Separated proteins were transferred to nitrocellulose membranes. The western blot was carried out with the anti-Stat3 and anti-phospho-Stat3 antibodies (Cell Signaling, Danvers, MA) or anti-β-actin antibody (Santa Cruz Biotechnology, Santa Cruz, CA).

CYTOKINE ASSAY. Culture supernatants were assessed for mIL-IL-1β using an ELISA kit (eBioscience, San Diego, CA).

QUANTITATIVE REAL-TIME PCR (QPCR). Relative quantification of select mRNA was performed using a CFX96 Realtime System and SsoFast™ Evagreen® supermixture (Bio-Rad Laboratories, Hercules, CA) according to the manufacturer's instructions. All primers were purchased from Eurofins MWG Operon (Huntsville, AL). Fold changes in mRNA expression between treatments and controls were determined by the $\Delta CT$ method (91). Fluorescence threshold cycle ($C_t$) values were calculated using SDS 700 System Software (Bio-Rad Laboratories, Hercules, CA). Results were normalized to the average $C_t$ for the GAPDH and β-actin housekeeping genes run in the QPCR. $\Delta\Delta C_t$ values were calculated to determine expression changes. Differences between groups were determined using a two sided Student's t-test and one-way ANOVA. Error bars on plots represent +/− standard error (SE), unless otherwise noted.

STATISTICAL ANALYSIS. Survival data were analyzed by log rank test. Student's t test was used for comparison of two samples with unequal variances. One-way ANOVA with Holm's post hoc test was used for comparing means of three or more variables.

Figure 7A:
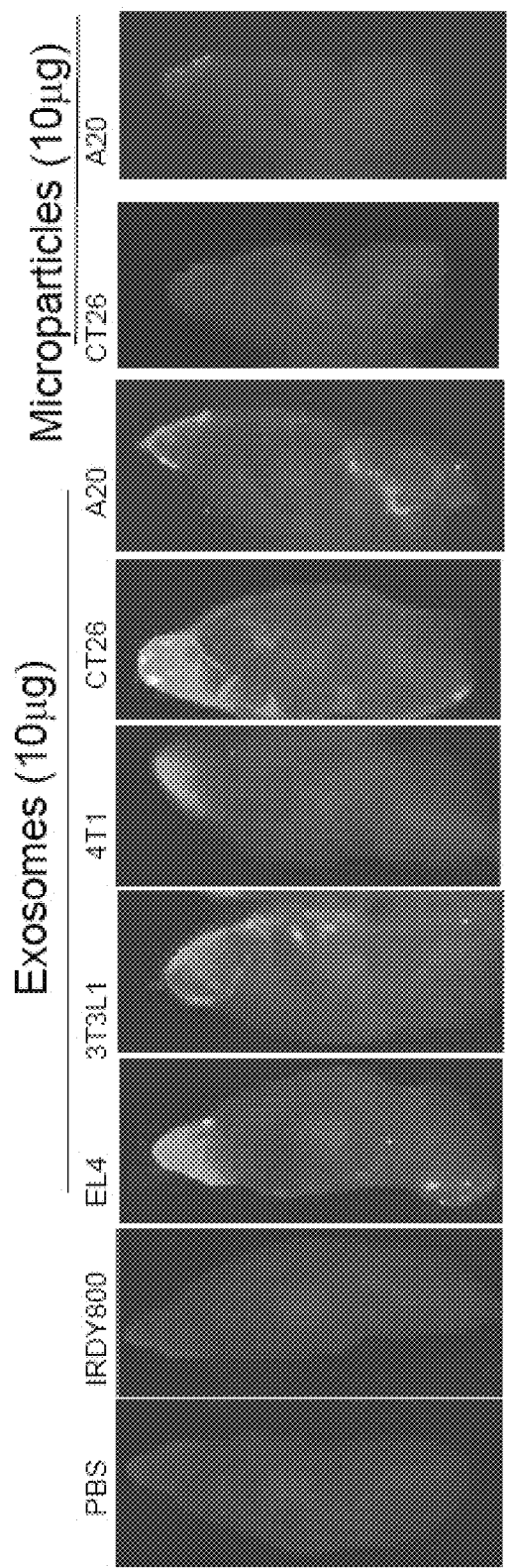
FIG. 7A includes images showing the distribution of fluorescently labeled exosomes in the brains of mice, where the images were taken 30 min after the exosomes were intranasally administered to the mice, and where the exosomes were isolated from various types of cells.
Figure 7B:
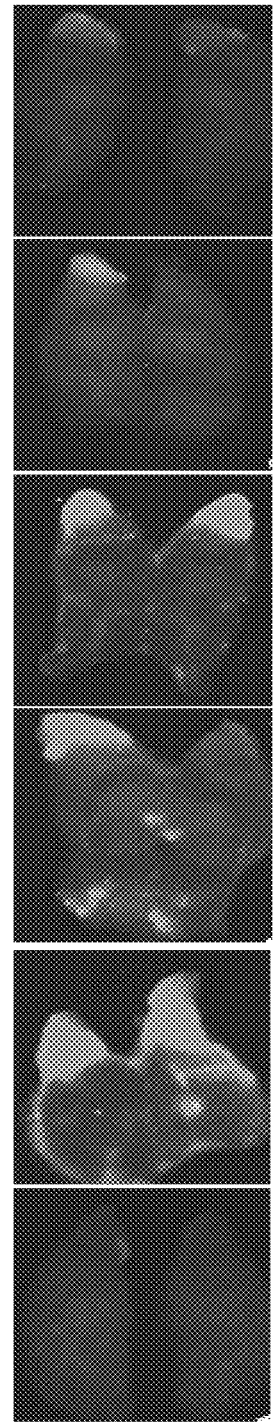
FIG. 7B includes images showing the distribution of fluorescently-labeled exosomes in the brains of mice, where the images were taken at 0, 3, 6, 12, 24, and 48 hours after the exosomes were intranasally administered to the mice, and where the exosomes were isolated from EL4 cells.

Example 5—Intranasally Administered Exosomes Rapidly Distributes Throughout the Brains of Mice To determine whether exosomes can be transported intranasally into the brain, Odyssey 800 dye-labeled exosomes were administered to non-tumor-bearing mice. Odyssey 800 dye-labeled exosomes (10 μg/10 μl) isolated from different types of cells (FIG. 7A) were administered as five doses of 2-μl drops spaced 2 min apart and one 2-μl drop into alternating sides of the nasal cavity with a small pipette. Mice were euthanized 30 min after intranasal delivery and their brains were examined for the presence of the exosomes using an Odyssey scanner. Fluorescent labeled exosomes were observed as being diffusely located in the brain with their primary location being in the olfactory bulb, suggesting that translocation of exosomes to the brain occurred rapidly (FIG. 7A). In contrast, no microparticles larger than exosomes were detected in the brain (FIG. 7A). Very little or no fluorescence was detected in the brain of mice intranasally administered PBS or free dye (FIG. 7A). These results indicate that particle size is a factor for translocation from the nasal region to the brain. No apparent toxicity or behavioral abnormalities were observed in any of the mice during and after (30 days) the experiment. The distribution of intranasal IRDye800-labeled exosomes in the brain was next investigated at various times after intranasal delivery of EL4 exosomes. Mice were given 10 μg IRDye800-labeled EL4 T cell derived exosomes over a 10-min time period as noted above, and then euthanized 3 to 48 h later. Fluorescence was stronger throughout the brain at 3 h after intranasal delivery, and remained visible at the olfactory bulb region of the brain 24 h after delivery (FIG. 7B). The animals did not exhibit any apparent toxicities or behavioral abnormalities during and after the course of this experiment.

Figure 8A:
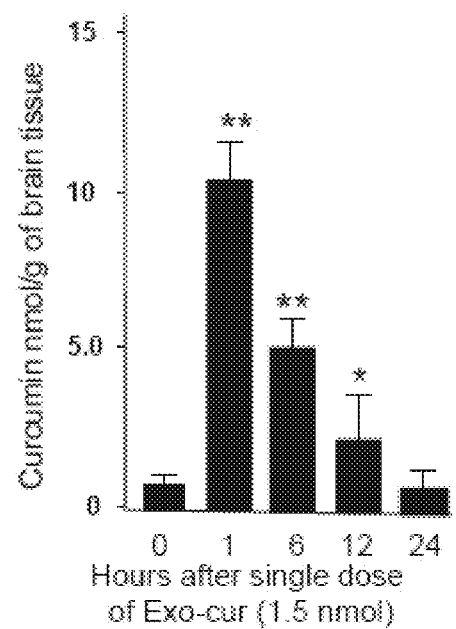
FIG. 8A is a graph showing the concentration of curcumin in the brain tissue of mice intranasally-administered a single dose of exosomal curcumin.
Figure 8B:
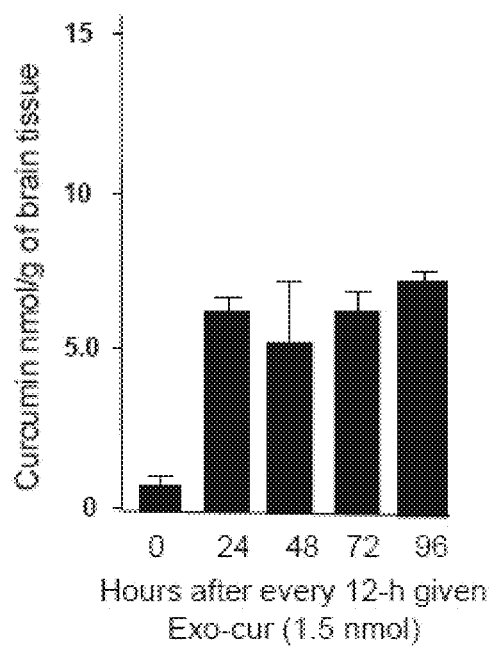
FIG. 8B is a graph showing the concentration of curcumin in the brains of mice intranasally-administered doses of exosomal curcumin every 12 hours.

Next, the capacity of exosomes to deliver curcumin to the brain was determined. The results of the quantification of curcumin intranasally delivered by EL4 exosomes (Exo-Cur) revealed that the curcumin reached peak concentrations 1 h after intranasal administration, and was still detectable in the olfactory bulb region within the first 12 h after a single intranasal administration of Exo-cur (FIG. 8A). Repeated administration of Exo-cur every 12 h maintained the curcumin concentration at an average of 5.6±1.2 nmol/g of brain tissue in the olfactory bulb region (FIG. 8B). Collectively, these data indicate that exosomes can be used as a novel non-invasive vehicle for delivery of therapeutic agents to the brain.

Figure 9:
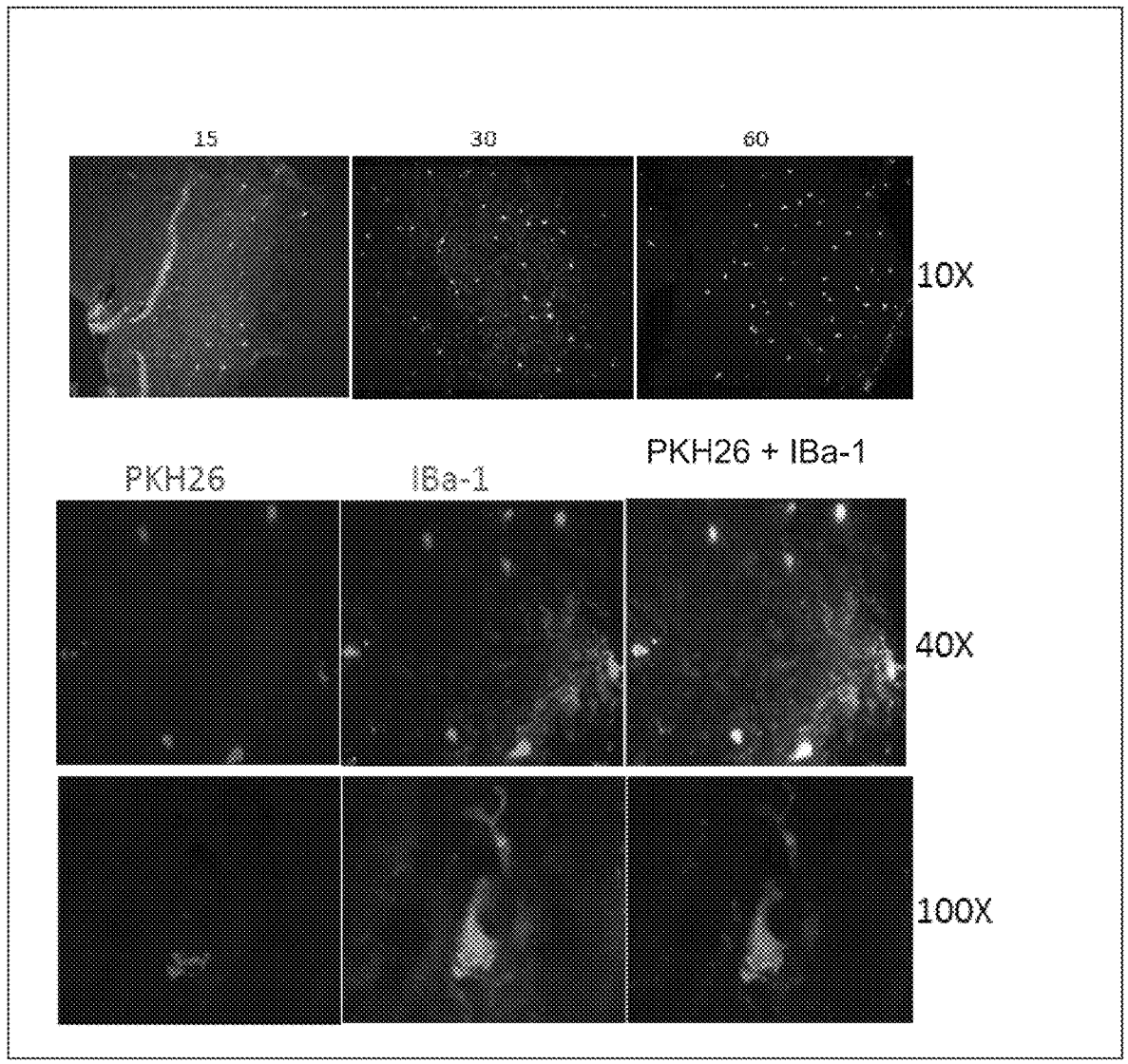
FIG. 9 includes images of brain sections of mice showing the presence of PHK26-labeled EL4 exosomes at 15, 30, and 60 minutes after the intranasal administration of the exosomes (upper images) and images of brain sections of mice showing the presence of PHK26-labeled exosomes in microglia cells as evidenced by the co-localization of the PHK26-labeled exosomes with the anti-microglia cell marker IBa-1 (lower images)

Example 6—Intranasally Delivered Exosomes Preferentially Accumulate in Microglia Cells To further identify specific targeting of cells by exosomes, in vivo biodistribution of fluorescent dye PKH26-labeled EL-4 exosomes was conducted. Double fluorescence positive cells evidenced by double positive PKH26$^+$Iba-1$^+$ cells (Iba-1 is a specific marker for microglia cells) were visible in brain microglia cells 15 min after intranasal delivery of exosomes, (FIG. 9A). Within an hour after injection, more than 80% of Iba-1$^+$ microglia cells were PHK26 positive (FIGS. 9A and 9B), indicating that the injected exosomes were taken up by the microglia cells.

Figure 10A:
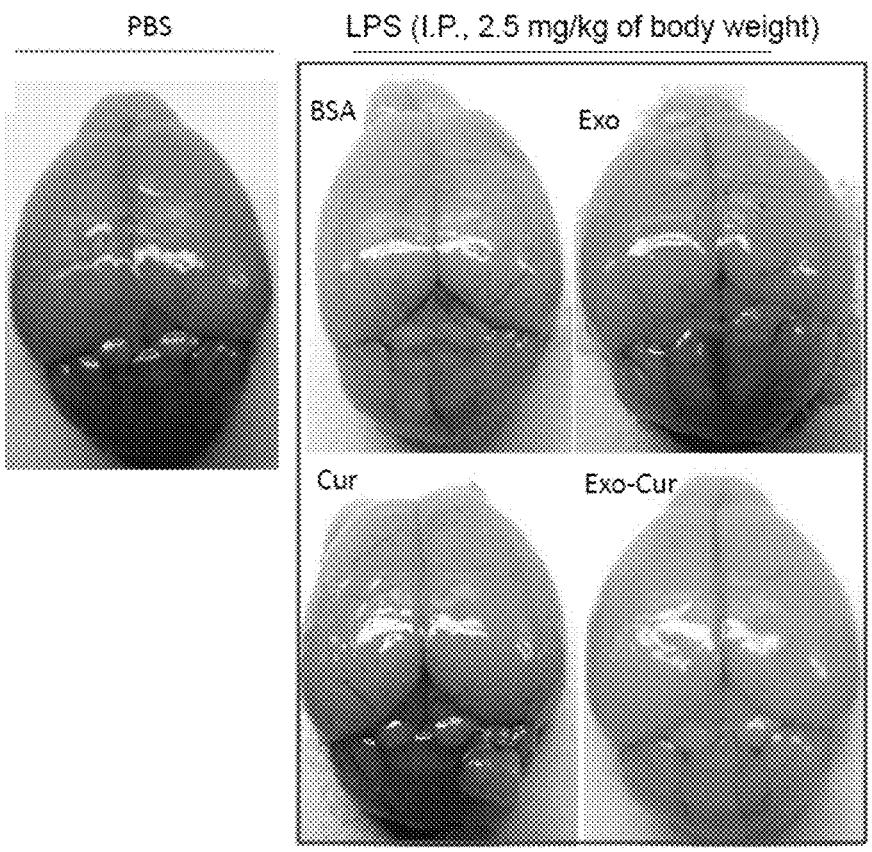
FIG. 10A includes images of mice brains where the mice were intraperitoneally injected with bacterial LPS (2.5. mg/kg) immediately prior to the intranasal administration of PBS, bovine serum albumin, EL4 exosomes, free curcumin, or exosomal curcumin.
Figure 10B:
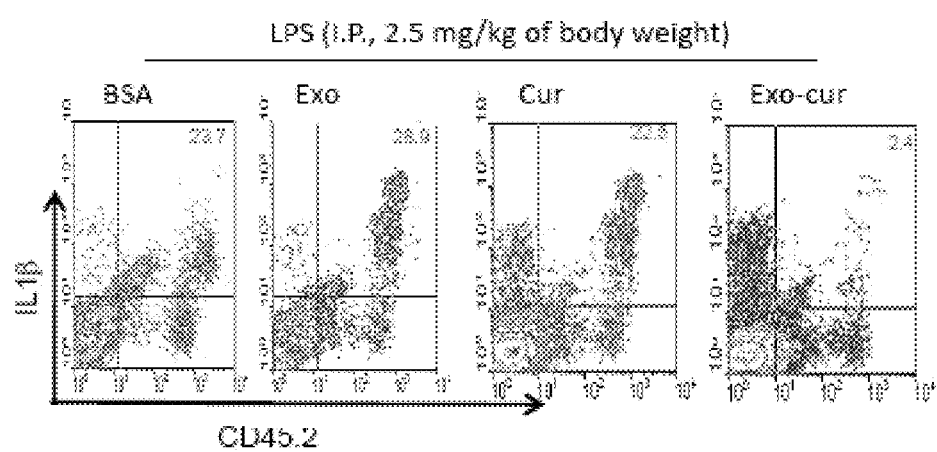
FIG. 10B includes graphs showing the FACS analysis of leukocytes isolated from the brains of mice two hours after the mice were intraperitoneally injected with bacterial LPS (2.5 mg/kg) immediately prior to the intranasal administration of PBS, bovine serum albumin, EL4 exosomes, free curcumin, or exosomal curcumin.
Figure 10C:
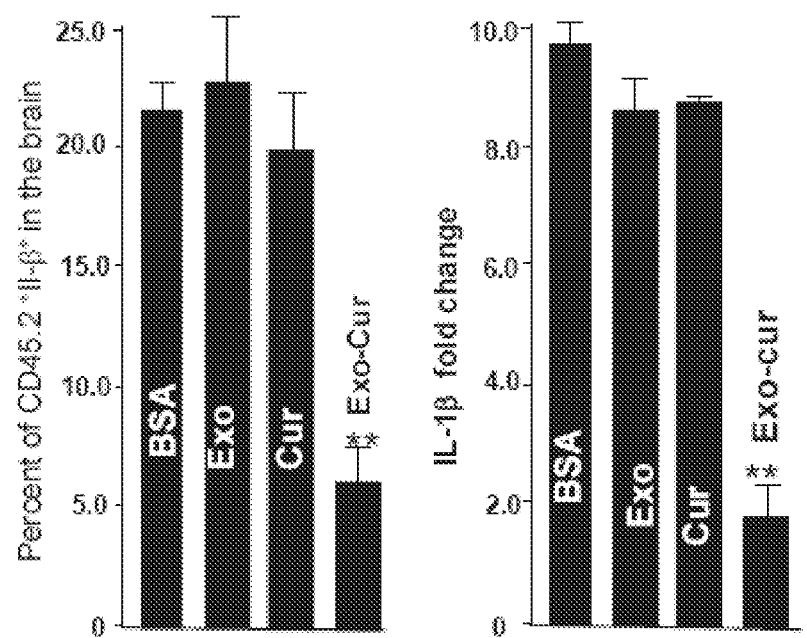
FIG. 10C includes graphs showing the percentage of $CD45.2^+IL-1\beta^+$ brain leukocytes and the quantitative real-time polymerase chain reaction (RT-PCR) analysis of IL-1β mRNA levels in mice intraperitoneally injected with bacterial LPS (2.5 mg/kg) immediately prior to the intranasal administration of PBS, bovine serum albumin, EL4 exosomes, free curcumin, or exosomal curcumin.
Figure 10D:
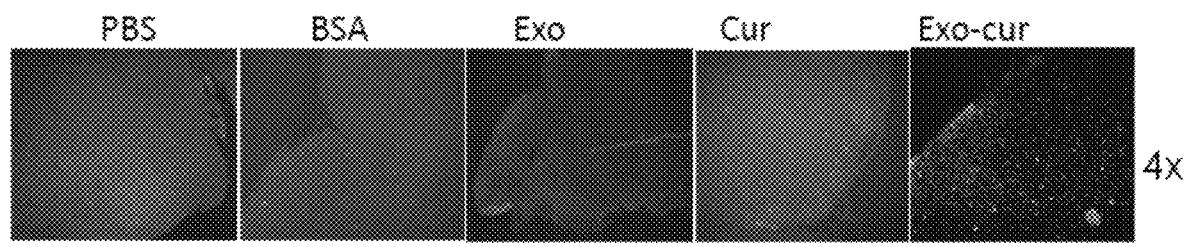
FIG. 10D includes terminal deoxynucleotidyl transferase dUTP nick end labeling (TUNEL)-stained images of frozen brain sections of mice intraperitoneally injected with bacterial LPS (2.5 mg/kg) immediately prior to the intranasal administration of PBS, bovine serum albumin, EL4 exosomes, free curcumin, or exosomal curcumin.
Figure 10E:
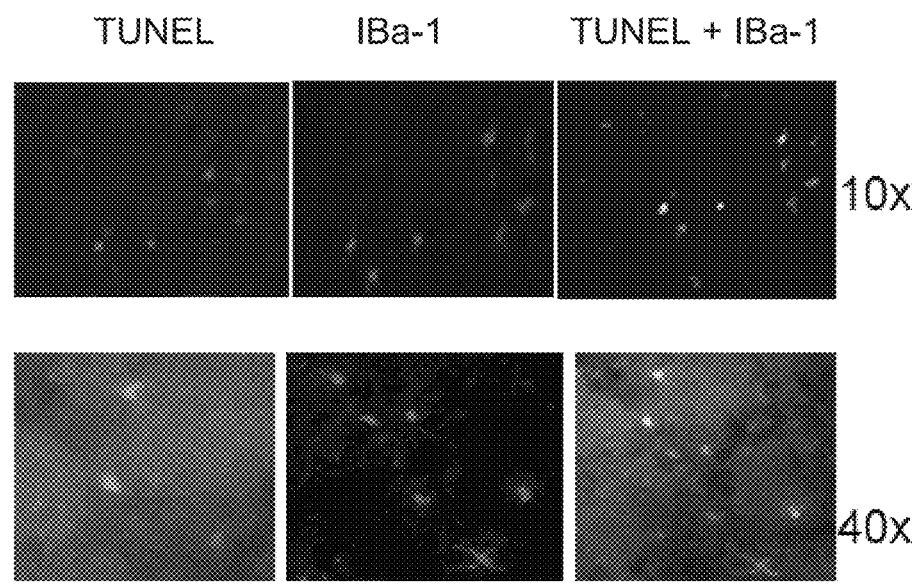
FIG. 10E includes images of brain leukocytes at 10× and 40× magnifications, where the brain leukocytes were isolated from mice 0.5, 1, 2, and 6 hours after the mice were intraperitoneally injected with bacterial LPS (2.5 mg/kg) and were then immediately intranasally-administered exosomal curcumin, and where the brain leukocytes were TUNEL-stained, anti-IBa-1-stained, or co-stained using both TUNEL and anti-IBa-1 staining.
Figure 10F:
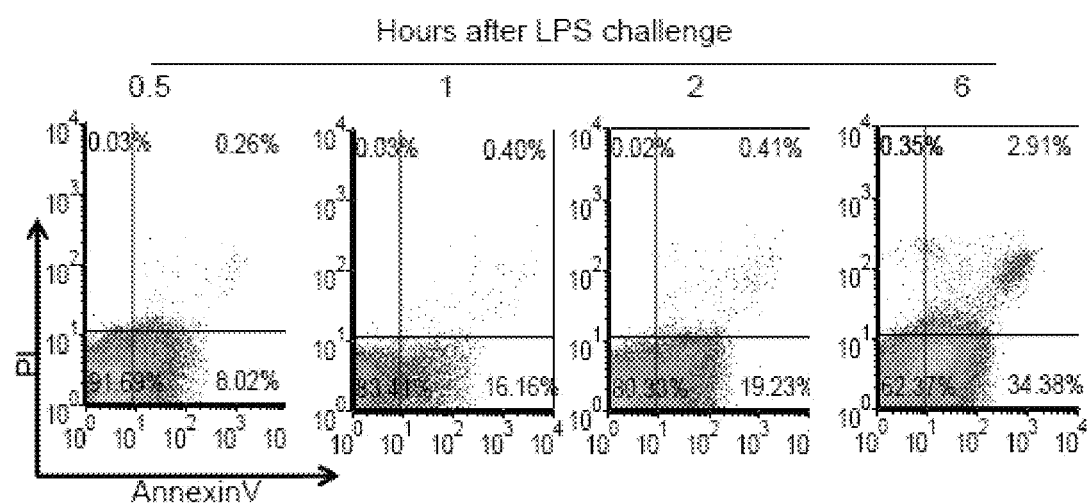
FIG. 10F includes images of FACS analysis of brain leukocytes from mice 0.5, 1, 2, and 6 hours after the mice were intraperitoneally injected with bacterial LPS (2.5 mg/kg) and were then immediately intranasally-administered exosomal curcumin, where the leukocytes were labeled with Annexin-V to identify apoptotic cells.
Figure 10G:
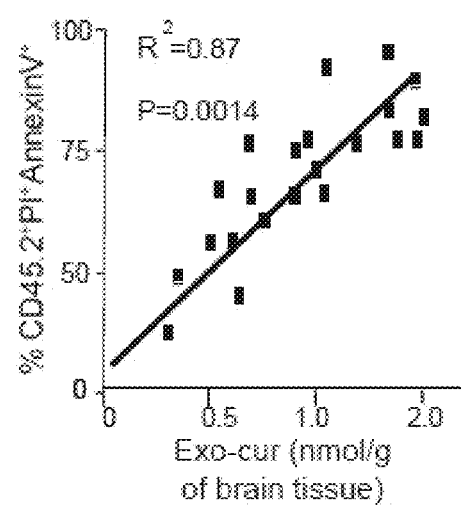
FIG. 10G is a graph showing the percentages of Annexin $V^+$ cells as a function of the concentration of exosomal curcumin in the brain tissue of mice that were intraperitoneally injected with bacterial LPS (2.5 mg/kg) immediately prior to the intranasal administration of exosomal curcumin.

Example 7—Exosome Encapsulated Curcumin Inhibits LPS Induced Brain Inflammation and MOG Induced Autoimmune Responses in an EAE Model Microglia cells have been shown to play a crucial role in brain inflammation. To determine whether the exosomes are functioning as a delivery vehicle to carry anti-inflammatory drugs, such as curcumin, and therefore treat brain inflammatory diseases, two independent disease models were tested. In the first model, intranasal administration of exosome encapsulated curcumin was used for treating LPS-challenged mice. The results indicate that 4 h after LPS challenge, mice receiving intranasal exosomal curcumin have reduced brain inflammation with less visible blood vessels (FIG. 10A) in comparison to other mice treated with either curcumin alone at the same dose as Exo-cur or exosomes alone. FACS analysis further indicated that the number of activated inflammatory microglia cells (CD45.2$^+$ IL-1β$^+$) was significantly reduced in the brain of mice that were treated intranasally with Exo-cur in comparison to the other treatments listed in FIG. 10B. The reduction of IL-1β in CD45.2 microglia cells was further confirmed by real-time PCR (FIG. 10C). The results of TUNEL staining of brain tissue indicated that Exo-cur treatment led to an increase in the number of apoptotic cells in mice administrated Exo-cur intranasally (FIG. 10D). Co-staining with a microglia cell-specific antibody (Iba-1 clone) (FIG. 10E) indicated that double positive cells (Tunel$^+$IBA-1$^+$) were microglia cells. The induction of apoptosis was further confirmed by the results of FACS analysis (FIG. 10F). The induction of apoptotic microglia cells correlated with the concentration of curcumin detected in the brain of mice treated with Exo-cur (FIG. 10G).

Figure 11A:
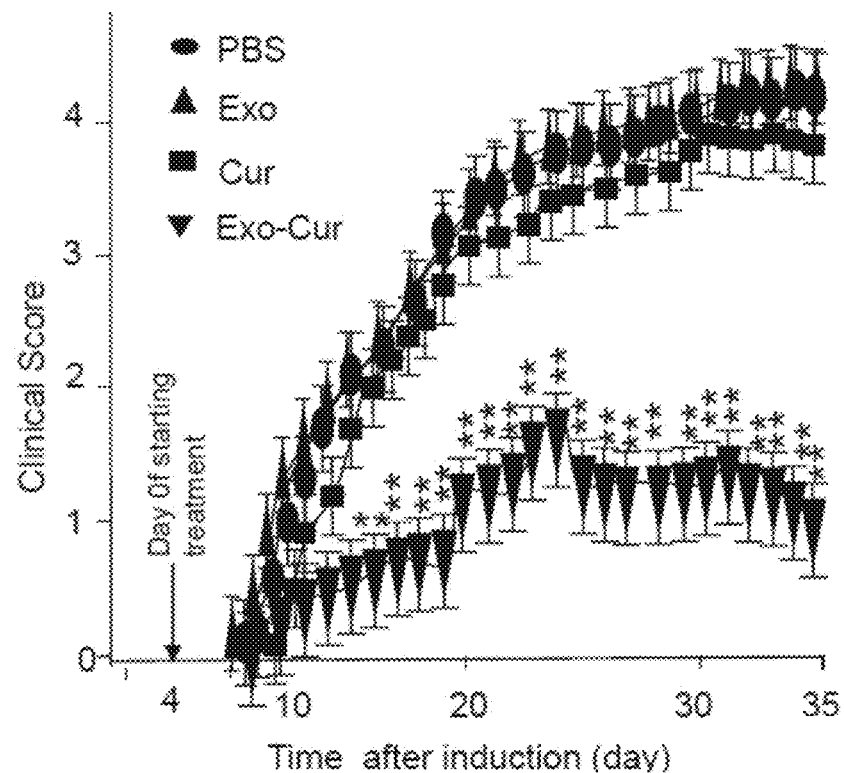
FIG. 11A is a graph showing the clinical scores for experimental autoimmune encephalitis (EAE) in mice that were administered a Myelin Oligodendrocyte Glycoprotein (MOG) 35-55 peptide to induce EAE and were then intranasally administered PBS, EL4 exosomes alone, curcumin, or exosomal curcumin starting 4 days after the administration of the MOG peptide and continuing until the mice were sacrificed at day 35 post MOG administration.
Figure 11B:
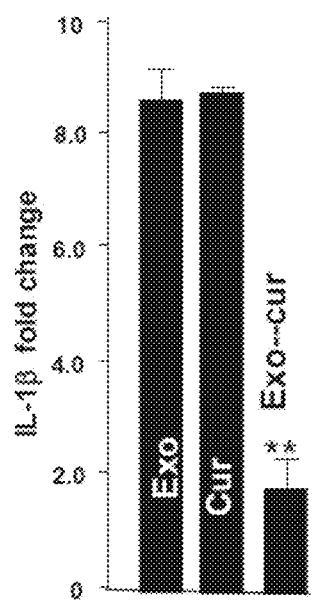
FIG. 11B is a graph showing the fold-change in IL-1β mRNA expression levels, as compared to a PBS control, in mice administered an MOG 35-55 peptide to induce EAE and then intranasally administered PBS, EL4 exosomes alone, curcumin, or exosomal curcumin.

To further determine if intranasal delivery of Exo-cur could prevent inflammation related brain autoimmune disease, MOG induced experimental autoimmune encephalomyelitis (EAE) in mice was utilized. EAE was induced in six-week-old female C57 BL/6 mice by immunization with MOG 35-55 as described previously (67). Exo-cur was administrated intranasally daily using the protocol described above and was initiated on day 4 after immunization with the MOG peptide until mice were sacrificed at day 35 post immunization. Disease severity was scored based on the method as described previously (67). The score of PBS, exosomes only, or curcumin only groups of EAE mice was 3.83±0.22, 3.70±0.31, and 3.60±0.12, respectively. The disease severity in Exo-cur treated mice was significantly reduced with a maximal disease severity score of 1.53±0.41 (FIG. 11A). Real-time PCR analysis also demonstrated that the expression of IL-1β in CD45.2 microglia cells was decreased significantly in the Exo-cur treated mice (FIG. 11B) in comparison with control groups.

Figure 12A:
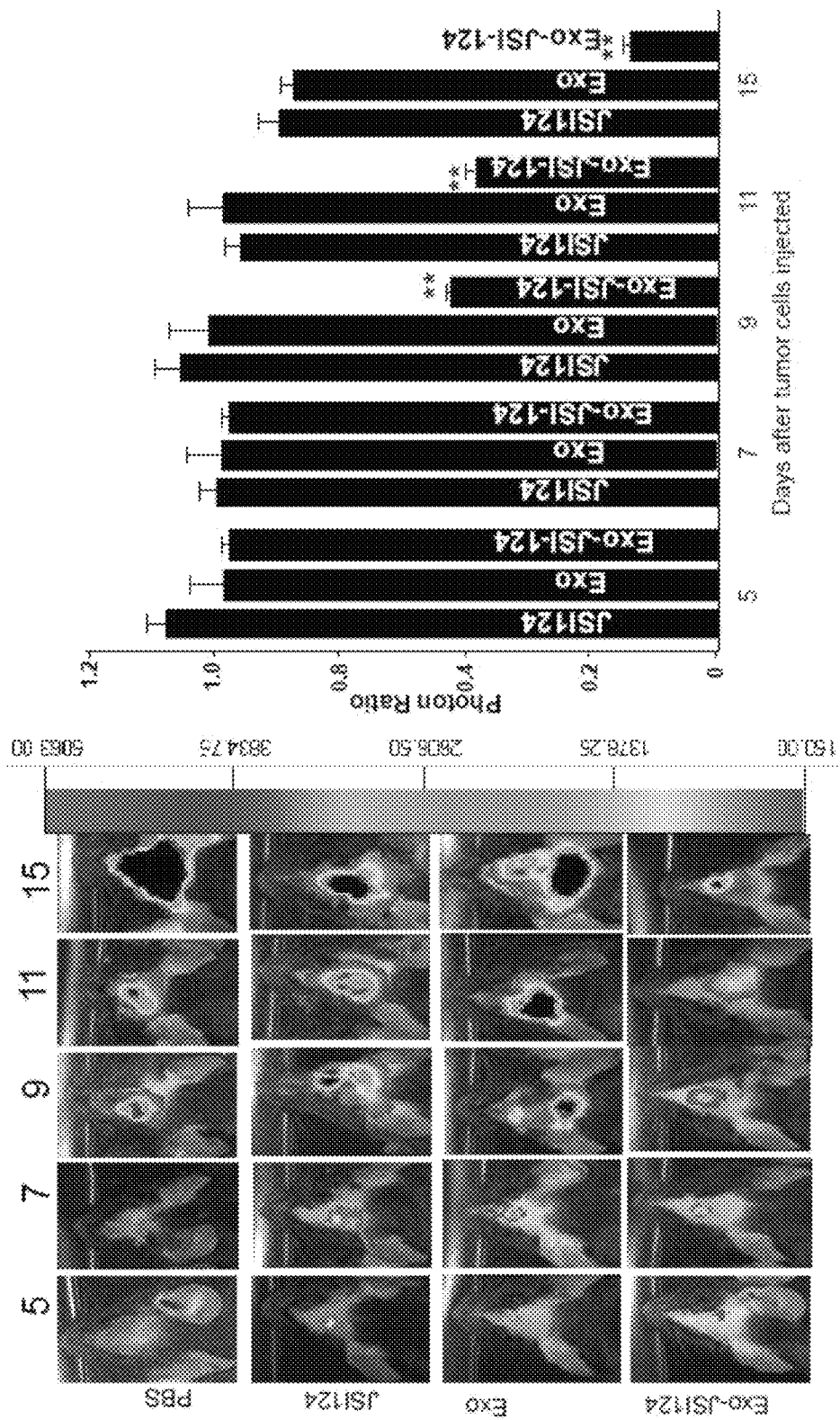
FIG. 12A includes images and a graph showing the photon emissions of mice injected with GL26 brain tumor cells and then intranasally administered PBS, EL4 exosomes alone, the Stat3 inhibitor JSI-124, or exosomal JSI-124.
Figure 12B:
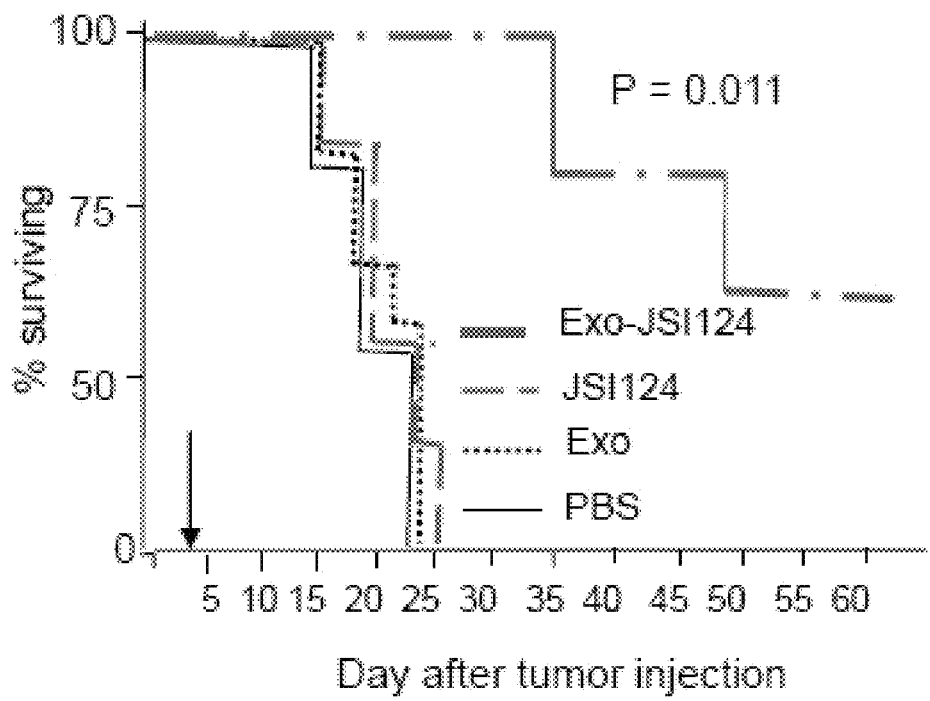
FIG. 12B is a graph showing the percentage of surviving mice after the mice were injected with GL26 brain tumor cells and then intranasally administered PBS, EL4 exosomes alone, the Stat3 inhibitor JSI-124, or exosomal JSI-124.
Figure 12C:
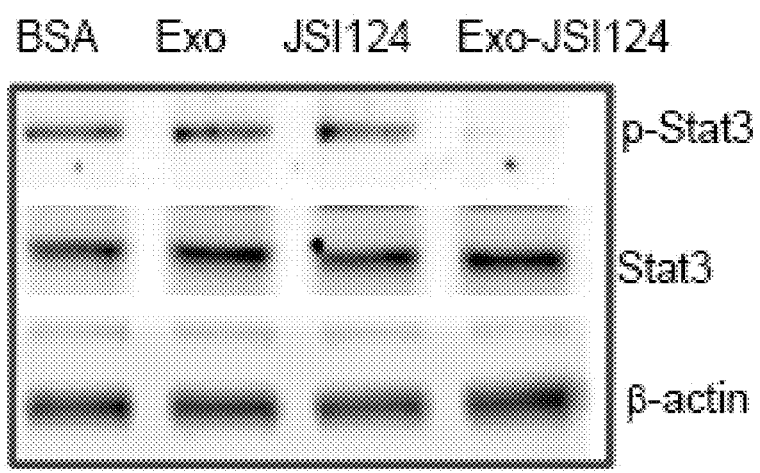
FIG. 12C is an image of a western blot for phospho-Stat3 in mice injected with GL26 brain tumor cells and then intranasally administered PBS, EL4 exosomes alone, the Stat3 inhibitor JSI-124, or exosomal JSI-124.
Figure 12D:
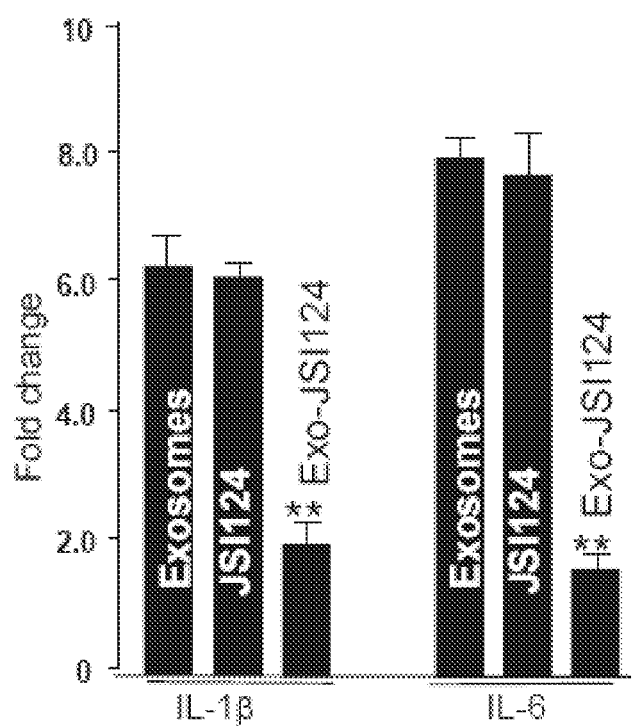
FIG. 12D is a graph showing the RT-PCR analysis of IL-1β and IL-6 mRNA levels in mice injected with GL26 brain tumor cells and then intranasally administered PBS, EL4 exosomes alone, the Stat3 inhibitor JSI-124, or exosomal JSI-124.

Example 8—Intranasal Delivery of an Exosome Encapsulated Stat3 Inhibitor Reduces GL26 Tumor Growth Signal transducer and activator of transcription 3 (Stat3) is activated constitutively in many types of human cancers and plays a critical role in tumor growth including microgliomas. Microglia cells, the resident macrophages of the brain, have been known to play a critical role in the progression of brain microglioma. To determine if exosome-encapsulated Stat3 inhibitors could be used to reduce the progression of brain microgliomas, groups of mice bearing intra-cerebral tumors were treated with exosome-encapsulated Stat3 inhibitor JSI-124 (12.5 pmol/10 μl) or exosomes only, JSI-124 only, or PBS as controls. Mice were treated every other day for 15 days beginning on day 3 after tumor cells were implanted. The amount of JSI-124 administered was based on the lack of any evidence of toxicity or behavioral abnormalities in the mice. Imaging data showed a statistically significant decrease in brain-associated photons in Exo-JSI-124 treated mice when compared to controls (FIG. 12A), and determined on day 9 after tumor cells were injected. Survival times of PBS-, exosomes- or JSI-124-control animals ranged from 20 to 25 days. In contrast, Exo-JSI-124 treatment significantly prolonged the survival of mice on the average of 44.5 days (p<0.011) (FIG. 12B). Moreover, two of the ten Exo-JSI-124 treated mice were alive and showed no neurological symptoms at day 90 when they were euthanized. There was no evidence of tumor at the original implantation site in these two mice. None of the Exo-JSI-124-treated animals exhibited evidence of toxicity or behavioral abnormalities during and after the 15-day treatment period. To further investigate if the observed effect was due to inhibition of Stat3 activity in the Exo-JSI-124 targeted cells in the brain, the activity of Stat3 in brain CD45.2$^+$ cells was quantitatively determined by western blot analysis of pStat3. The results indicated that Exo-JSI-124 treatment led to the selective reduction of pStat3 in CD45.2$^+$ microglia cells (FIG. 12C). The reduction of Stat3 was also correlated with a decrease in the expression of both IL-1β and IL-6 in CD45.2$^+$ microglia cells (FIG. 12D). Collectively, these data indicated that Exo-JSI-124 is selectively taken up by microglia cells and subsequently inhibits the expression of inflammatory cytokines such as IL-1β and IL-6.

Discussion of Examples 5-8

The blood-brain barrier has been an obstacle to the development of CNS therapeutics, impeding clinical use of otherwise promising therapeutic agents in the treatment of many brain neuron disorders, where inflammation plays a causative role. Despite these previous obstacles, the experiments described in the foregoing examples 5-8 examined a novel approach for intranasal delivery of therapeutic agents to the brain. The results of those experiments indicated that anti-inflammatory agents like curcumin or JSI-124 were effectively delivered to the brain by exosomes without observable side effects. Furthermore, microglia cells were identified as being preferentially targeted by exosomes. The successful delivery and therapeutic effects of curcumin or JSI-124 loaded exosomes was demonstrated in three independent mouse models, i.e., a LPS induced brain inflammation model, MOG induced EAE autoimmune disease, and a GL26 implanted brain tumor model. Microglia cells are well-known to play an essential role in many inflammatory related brain diseases. The accumulation of myeloid or microglia cells in the brain has been implicated in the promotion of brain tumor growth and progression of brain autoimmune diseases, such as EAE in mouse models and in humans (68-79). In the experiments described in Examples 5-8, it was found that intranasal administration of Exo-cur or Exo-JSI-124 led to a significant reduction in the number of microglia cells and a concomitant reduction in disease progression in all three models we tested. These findings are also consistent with the results described in Examples 1-4 showing that inflammatory cells such as $CD11b^+Gr-1^+$ cells, can be deleted specifically by curcumin encapsulated in exosomes. In Examples 1-4, it was demonstrated that mice treated with Exo-cur are protected completely against LPS-induced septic shock and that the protective mechanism is associated with the ability of the Exo-cur to specifically target myeloid cells. Without wishing to be bound by any particular theory, it was thus thought that the strategy of delivering exosome encapsulated drugs to the brain via intranasal administration could potentially improve the direct delivery of drugs to the CNS with the advantages of target specificity and administration in a non-invasive manner. In this regard, the foregoing data show that curcumin encapsulated in exosomes not only targets to inflammatory cells, i.e., microglia cells, but reaches the CNS in sufficient quantity by this route to be effective.

In summary, the foregoing results indicate that direct intranasal-to-brain transport is feasible. Additionally, rapid movement of exosomes into the brain was found within 1 hour. This finding is consistent with the extraneuronal pathway that has been proposed for transport of therapeutic agents from the nasal cavity to the brain (52-53). Transport occurs along the olfactory pathway and likely involves extracellular bulk flow along perineuronal and/or perivascular channels, which delivers drug directly to the brain parenchyma. Delivery along the extraneuronal pathway is likely not receptor-mediated and requires only minutes for a therapeutic agent to reach the brain; whereas, delivery via an intraneuronal pathway along the primary olfactory sensory neurons involves axonal transport and requires several days for the drug to reach different areas of the brain (80, 81).

Example 9—Preparation of Exosomes Incorporating Additional Phytochemical Agents or Chemotherapeutic Drugs Exosomes including the phytochemical agents resveratrol, baicalein, equol, fisetin, quercetin, or exosomes including the chemotherapeutic agents retinoic acid, 5-fluorouracil, vincristine, actinomycin D, adriamycin, cisplatin, docetaxel, doxorubicin, or taxol are prepared by mixing the one or more of the phytochemical agents or chemotherapeutic agents with exosomes in PBS. After incubation at 22° C. for 5 minutes, the mixture is subjected to a sucrose gradient (8, 30, 45, and 60%, respectively) and then centrifugation for 1.5 hours at 36,000 rpm. The exosomal phytochemical agents or chemotherapeutic drugs band in the sucrose gradient between 45 and 60%, and are subsequently collected, washed, and dissolved with PBS. The aliquots are then stored at −80° C. until use.

Example 10—Use of Exosomes or Exosomal Phytochemical Agents or Chemotherapeutic Agents for Treatment of Colon Cancer Mice, 6-8 wk of age, are injected intraperitoneally with 10 mg/kg azoxymethane (AOM) in 0.2 ml PBS. 1 week after AOM administration, dextran sulfate sodium (DSS) at 2% is administered in the drinking water for five consecutive days. Thereafter, mice received reverse osmosis water. Up to four DSS cycles are administered with intervals of 16 d on water between cycles. The mice are gavage-administrated with exosomes or exosomal phytochemical agents or chemotherapeutic agent in 0.3 ml PBS. Mice are treated daily for 3 weeks. Mice are monitored for body weight, rectal prolapse, diarrhea, and macroscopic bleeding, as well as occult blood by hemoccult (Beckman Coulter, Brea, CA). After the mice are sacrificed, the colons are resected, flushed with PBS, opened longitudinally, and measured. Polyps are then counted using a stereomicroscope and colon sections are fixed in formalin or snap frozen. Upon analysis of the results of these experiments, it is observed that mice administered exosomal phytochemical agents or chemotherapeutic agents have a lower number of polyps as compared to control mice, indicating that the exosomal phytochemical or chemotherapeutic agents can successfully be administered as part of a method for treating colon cancer.

Throughout this document, various references are mentioned. All such references are incorporated herein by reference, including the references set forth in the following list:

REFERENCES

1. Papazoglou E S, Parthasarathy A: Bionanotechnology, Morgan & Claypool Publisher, 1-43 (2007).
2. N.N.i. Nanotechnology: What is Nanotechnology? (2000).
3. Gradishar W J, Tjulandin S, Davidson N, et al. Phase III trial of nanoparticle albumin-bound paclitaxel compared with polyethylated castor oil-based paclitaxel in women with breast cancer. *J. Clin. Oncol.* 23, 7794-7803 (2005).
4. Bhatt R, de Vries P, Tulinsky J, et al. Synthesis and in vivo antitumor activity of poly(1-glutamic acid) conjugates of 20S-camptothecin. *J. Med. Chem.* 46, 190-193 (2003).
5. Markman M. Pegylated liposomal doxorubicin in the treatment of cancer of the breast and ovary. *Expert Opin. Pharmacother* 7, 1469-1474 (2006).
6. Rosenthal E, Poizot-Martin I, Saint-Marc T, et al. Phase IV study of liposomal daunorubicin (DaunoXome) in AIDS-related kaposi sarcoma. *Am. J. Clin. Oncol.* 25, 57-59 (2002).
7. Lacerda S H, Park J J, Meuse C. et al: Interaction of gold nanoparticles with common human blood proteins. *ACS Nano* (2009).
8. Pastorin G, Wu W, Wieckowski S, et al. Double functionalisation of carbon nanotubes for multimodal drug delivery. *Chem. Commun.* 11, 1182-1194 (2006).
9. Patnaik S, Mohammad A, Pathak A, Kurupati R, Singh Y, Gupta K C. Cross-linked polyethylenimine-hexametaphosphate nanoparticles to deliver nucleic acids therapeutics. *Nanomedicine* 2009 Aug. 20. [Epub ahead of print]
10. Yagi N, Manabe I, Tottori T, et al. A nanoparticle system specifically designed to deliver short interfering RNA inhibits tumor growth in vivo. *Cancer Res.* 69(16), 6531-6538 (2009).
11. Karatas H, Aktas Y, Gursoy-Ozdemir Y. et al. A nanomedicine transports a peptide caspase-3 inhibitor across the blood-brain barrier and provides neuroprotection. *J. Neurosci.* 29(44), 13761-13769 (2009).
12. Li X, Zhang Z, Beiter T, Schluesener H J. Nanovesicular vaccines: exosomes. *Arch. Immunol. Ther. Exp.* 53(4), 329-335 (2005).

13. van Niel G, Porto-carreiro I, Simoes S, Raposo G. Exosomes: A common pathway for a specialized function. *J. Biochem.* 140(1), 13-21 (2006).
14. Anand P, Thomas S G, Kunnumakkara A B. et al. Biological activities of curcumin and its analogues (Congeners) made by man and Mother Nature. *Biochem. Pharmacol.* 76(11), 1590-1611 (2008).
15. Anand P, Kunnumakkara A B, Newman R A, Aggarwal B B. Bioavailability of curcumin: problems and promises. *Mol. Pharm.* 4(6), 807-818 (2007).
16. Shoba G, Joy D, Joseph T, Majeed M, Rajendran R, Srinivas P S. Influence of piperine on the pharmacokinetics of curcumin in animals and human volunteers. *Planta. Med.* 64(4), 353-356 (1998) Friedman L, Lin L, Ball S. et al. Curcumin analogues exhibit enhanced growth suppressive activity in human pancreatic cancer cells. *Anticancer Drugs* 20(6), 444-449 (2009).
18. Tham C L, Liew C Y, Lam K W. et al. A synthetic curucuminoid derivative inhibits nitric oxide and proinflammatory cytokine synthesis. *Eur. J. Pharmacol.* (Epub ahead of print).
19. Li L, Braiteh F S, Kurzrock R. Liposome-encapsulated curcumin: In vitro and in vivo effects on proliferation, apoptosis, signaling, and angiogenesis. *Cancer* 104(6), 1322-1331 (2005).
20. Shaikh J, Ankola D D, Beniwal V, Singh D, Kumar M N. Nanoparticle encapsulation improved oral bioavailability of curcumin by at least 9-fold when compared to curcumin administered with piperine as absorption enhancer. *Eur. J. Pharm. Sci.* 37(3-4), 223-230 (2009).
21. Cao F L, Xi Y W, Tang L, Yu A H, Zhai G X. Preparation and characterization of curcumin loaded gelatin microspheres for targeting. *Zhong Yao Cai* 32 (3), 423-426 (2009)
22. Liu C, Yu S, Zinn K. et al. Murine mammary carcinoma exosomes promote tumor growth by suppression of N K cell function. *J. Immunol.* 176 (3), 1375-1385 (2006).
23. Wang G J, Liu Y, Qin A. et al. Thymus exosomes-like particles induce regulatory T cells. *J. Immunol.* 181 (8), 5242-5248 (2008).
24. Li J, Jiang Y, Wen J, Fan G, Wu Y, Zhang C. A rapid and simple HPLC method for the determination of curcumin in rat plasma: assay development, validation and application to a pharmacokinetic study of curcumin liposome. *Biomed. Chromatogr.* 23 (11), 1201-1207 (2009).
25. Xiang X, Poliakov A, Liu C. et al. Induction of myeloid-derived suppressor cells by tumor exosomes. *Int. J. Cancer* 124 (11), 2621-2633 (2009).
26. Medoff B D, Seung E, Hong S. et al. CD11b+ myeloid cells are the key mediators of Th2 cell homing into the airway in allergic inflammation. *J. Immunol.* 182, 623-635 (2009).
27. Hoogerwerf J J, de Vos A F, Bresser P. et al. Lung inflammation induced by lipoteichoic acid or lipopolysaccharide in humans. *Am. J. Respir. Crit. Care Med.* 178 (1), 34-41 (2008).
28. Valenti R, Huber V, Filipazzi P. et al. Human tumor-released microvesicles promote the differentiation of myeloid cells with transforming growth factor-beta-mediated suppressive activity on T lymphocytes. *Cancer Res.* 66 (18), 9290-9298 (2006).
29. Cho K, Wang X, Nie S, Chen Z G, Shin D M. Therapeutic nanoparticles for drug delivery in cancer. *Clin. Cancer Res.* 14 (5), 1310-1316 (2008).
30. Choi H S, Ipe B I, Misra P, Lee J H, Bawendi M G, Frangioni J V. Tissue- and organ-selective biodistribution of NIR fluorescent quantum dots. *Nano Lett.* 9 (6), 2354-2359 (2009).
31. Wagner V, Dullaart A, Bock A, Zweck A. The emerging nanomedicine landscape. *Nat. Biotech.* 24, 1211-1217 (2006).
32. Narayanan N K, Nargi D, Randolph C, Narayanan B A. Liposome-encapsulation of curcumin and resveratrol in combination reduced prostate cancer incidence in PTEN knockout mice. *Int. J. Cancer* 125, 1-8 (2009).
33. Li L, Ahmed B, Mehta K, Kurzrock R. Liposomal curcumin with and without oxaliplatin: effects on cell growth, apoptosis, and angiogenesis in colorectal cancer. *Mol Cancer Ther.* 6, 1276-1282 (2007)
34. Maiti K, Mukherjee K, Gantait A, Saha B P, Mukherjee P K. Curcumin-phospholipid complex: Preparation, therapeutic evaluation and pharmacokinetic study in rats. *Int. J. Pharm.* 330, 155-163 (2007).
35. Figg W D, Folkman J. Angiogenesis: An integrative approach from science to medicine. Chapter 2: *Angiogenesis and vascular remodeling in inflammation and cancer*. Mcdonald D M. 17-35 (2008).
36. Krishna A D, Mandraju R K, Kishore G, Kondapi A K. An efficient targeted drug delivery through apotransferrin loaded nanoparticles. *Plos One* 4(10), e7240 (2009).
37. Zhang X, Koh C G, Yu B. et al. Transferrin receptor targeted lipopolyplexes for delivery of antisense oligonucleotide g3139 in a murine k562 xenograft model. *Pharm. Res.* 26(6), 1516-1524 (2009).
38. Andre F, Chaput N, Schartz N E. et al. Exosomes as potent cell-free peptide-based vaccine. I. Dendritic cell-derived exosomes transfer functional MHC class I/peptide complexes to dendritic cells. *J. Immunol.* 172 (4), 2126-2136 (2004).
39. Chaput N, Schartz N E, Andre F. et al. Exosomes as potent cell-free peptide-based vaccine. II. Exosomes in CpG adjuvants efficiently prime naive Tc1 lymphocytes leading to tumor rejection. *J. Immunol.* 172 (4), 2137-2146 (2004).
40. Wolfers J, Lozier A, Raposo G. et al. Tumor-derived exosomes are a source of shared tumor rejection antigens for CTL cross-priming. *Nat. Med.* 7(3), 297-303 (2001).
41. Miyanishi M, Tada K, Koike M, Uchiyama Y, Kitamura T, Nagata S. Identification of Tim4 as a phosphatidylserine receptor. *Nature* 450, 435-439 (2007).
42. Fuller A D and Van Eldik L J. MFG-E8 regulates microglial phagocytosis of apoptotic neurons. *J. Neuroimmune Pharmacol.* 3, 246-256 (2008).
43. Peter C, Waibel M, Radu C G, et al. Migration to apoptotic "find me" signals is mediated via the phagocyte receptor G2A. *J. Biol. Chem.* 283, 5296-5305 (2008).
44. Yoshida H, Kawane K, Koike M, Mori Y, Uchiyama Y, Nagata S. Phosphatidylserine-dependent engulfment by macrophages of nuclei from erythroid precursor cells. *Nature* 437, 754-758 (2005).
45. Parente L and Solito E. Annexin 1: more than an anti-phospholipase protein. *Inflamm. Res.* 53, 125-132 (2004).
46. Savill J, Gregory C, and Haslett C. Cell biology: Eat me or die. *Science* 302, 1516-1517 (2003).
47. Depraetere V. "Eat me" signals of apoptotic bodies. *Nat. Cell Biol.* 2, E104 (2000).
48. Dai S, Wei D, Wu Z. et al. Phase I clinical trial of autologous ascites-derived exosomes combined with G M-CSF for colorectal cancer. *Mol. Ther.* 16(4), 782-790 (2008).

49 Escudier B, Dorval T, Chaput N. et al. Vaccination of metastatic melanoma patients with autologous dendritic cell (DC) derived-exosomes: results of the first phase I clinical trial. *J. Transl. Med.* 3(1), 10 (2005).

50. Navabi H, Croston D, Hobot J. et al. Preparation of human ovarian cancer ascites-derived exosomes for a clinical trial. *Blood cells Mol. Dis.* 35(2), 149-152 (2005).

51. Hossain, S., Akaike, T. & Chowdhury, E. H. Current Approaches for Drug Delivery to Central Nervous System. *Curr Drug Deliv.*

52. Soni, V., Jain, A., Khare, P., Gulbake, A. & Jain, S. K. Potential approaches for drug delivery to the brain: past, present, and future. *Crit Rev Ther Drug Carrier Syst* 27, 187-236.

53. Potschka, H. Targeting the brain—surmounting or bypassing the blood-brain barrier. *Handb Exp Pharmacol*, 411-431.

54. Carvey, P. M., Hendey, B. & Monahan, A. J. The blood-brain barrier in neurodegenerative disease: a rhetorical perspective. *J Neurochem* 111, 291-314 (2009).

55. Gabathuler, R. Blood-brain barrier transport of drugs for the treatment of brain diseases. *CNS Neurol Disord Drug Targets* 8, 195-204 (2009).

56. Bidros, D. S. & Vogelbaum, M. A. Novel drug delivery strategies in neuro-oncology. *Neurotherapeutics* 6, 539-546 (2009).

57. Yang, I., Han, S. J., Kaur, G., Crane, C. & Parsa, A. T. The role of microglia in central nervous system immunity and glioma immunology. *J Clin Neurosci* 17, 6-10.

58. Yadav, A. & Collman, R. G. CNS inflammation and macrophage/microglial biology associated with HIV-1 infection. *J Neuroimmune Pharmacol* 4, 430-447 (2009).

59. Choi, J. & Koh, S. Role of brain inflammation in epileptogenesis. *Yonsei Med J* 49, 1-18 (2008).

60. Rock, R. B. & Peterson, P. K. Microglia as a pharmacological target in infectious and inflammatory diseases of the brain. *J Neuroimmune Pharmacol* 1, 117-126 (2006).

61. Johnson, N. J., Hanson, L. R. & Frey, W. H. Trigeminal pathways deliver a low molecular weight drug from the nose to the brain and orofacial structures. *Mol Pharm* 7, 884-893.

62. Garcia-Rodriguez, J. C. & Sosa-Teste, I. The nasal route as a potential pathway for delivery of erythropoietin in the treatment of acute ischemic stroke in humans. *Scientific World Journal* 9, 970-981 (2009).

63. Mistry, A., Stolnik, S. & Illum, L. Nanoparticles for direct nose-to-brain delivery of drugs. *Int J Pharm* 379, 146-157 (2009).

64. Wu, H., Hu, K. & Jiang, X. From nose to brain: understanding transport capacity and transport rate of drugs. *Expert Opin Drug Deliv* 5, 1159-1168 (2008).

65. Kastin, A. J. & Pan, W. Intranasal leptin: blood-brain barrier bypass (BBBB) for obesity? *Endocrinology* 147, 2086-2087 (2006).

66 Sun, D. et al. A novel nanoparticle drug delivery system: the anti-inflammatory activity of curcumin is enhanced when encapsulated in exosomes. *Mol Ther* 18, 1606-1614.

67. Axtell, R. C. et al. T helper type 1 and 17 cells determine efficacy of interferon-beta in multiple sclerosis and experimental encephalomyelitis. *Nat Med* 16, 406-412.

68. Graler, M. H. Targeting sphingosine 1-phosphate (S1P) levels and S1P receptor functions for therapeutic immune interventions. *Cell Physiol Biochem* 26, 79-86.

69 Shelton, R. C. & Miller, A. H. Eating ourselves to death (and despair): the contribution of adiposity and inflammation to depression. *Prog Neurobiol* 91, 275-299.

70 Scott, K. F. et al. Emerging roles for phospholipase A2 enzymes in cancer. *Biochimie* 92, 601-610.

71. Choi, J. W. et al. LPA receptors: subtypes and biological actions. *Annu Rev Pharmacol Toxicol* 50, 157-186.

72. Berquin, I. M., Edwards, I. J. & Chen, Y. Q. Multi-targeted therapy of cancer by omega-3 fatty acids. *Cancer Lett* 269, 363-377 (2008).

73. Murakami, A. & Ohigashi, H. Targeting NOX, INOS and COX-2 in inflammatory cells: chemoprevention using food phytochemicals. *Int J Cancer* 121, 2357-2363 (2007).

74 Harizi, H. & Gualde, N. Pivotal role of PGE2 and IL-10 in the cross-regulation of dendritic cell-derived inflammatory mediators. *Cell Mol Immunol* 3, 271-277 (2006).

75 Kuhn, H. & O'Donnell, V. B. Inflammation and immune regulation by 12/15-lipoxygenases. *Prog Lipid Res* 45, 334-356 (2006).

76. Frey, A. B. Myeloid suppressor cells regulate the adaptive immune response to cancer. *J Clin Invest* 116, 2587-2590 (2006).

77. Huang, B. et al. Gr-1+CD115+ immature myeloid suppressor cells mediate the development of tumor-induced T regulatory cells and T-cell anergy in tumor-bearing host. *Cancer Res* 66, 1123-1131 (2006).

78. Kusmartsev, S. & Gabrilovich, D. I. Immature myeloid cells and cancer-associated immune suppression. *Cancer Immunol Immunother* 51, 293-298 (2002).

79 Kusmartsev, S. & Gabrilovich, D. I. Inhibition of myeloid cell differentiation in cancer: the role of reactive oxygen species. *J Leukoc Biol* 74, 186-196 (2003).

80 Thorne, R. G., Emory, C. R., Ala, T. A. & Frey, W. H., 2nd Quantitative analysis of the olfactory pathway for drug delivery to the brain. *Brain Res* 692, 278-282 (1995).

81. Balin, B. J., Broadwell, R. D., Salcman, M. & el-Kalliny, M. Avenues for entry of peripherally administered protein to the central nervous system in mouse, rat, and squirrel monkey. *J Comp Neurol* 251, 260-280 (1986).

82. Wang, G. J. et al. Thymus exosomes-like particles induce regulatory T cells. *J Immunol* 181, 5242-5248 (2008).

83. Wang, J. et al. JAB1 determines the response of rheumatoid arthritis synovial fibroblasts to tumor necrosis factor-alpha. *Am J Pathol* 169, 889-902 (2006).

84. Alizadeh, D. et al. Induction of anti-glioma natural killer cell response following multiple low-dose intracerebral CpG therapy. *Clin Cancer Res* 16, 3399-3408.

85. Liu, C. et al. Expansion of spleen myeloid suppressor cells represses NK cell cytotoxicity in tumor-bearing host. *Blood* 109, 4336-4342 (2007).

86. Zhang, H. G. et al. Gene therapy that inhibits nuclear translocation of nuclear factor kappaB results in tumor necrosis factor alpha-induced apoptosis of human synovial fibroblasts. *Arthritis Rheum* 43, 1094-1105 (2000).

87. Liu, Z. et al. CII-D C-AdTRAIL cell gene therapy inhibits infiltration of CII-reactive T cells and CII-induced arthritis. *J Clin Invest* 112, 1332-1341 (2003).

88. Zhang, H. G. et al. Novel tumor necrosis factor alpha-regulated genes in rheumatoid arthritis. *Arthritis Rheum* 50, 420-431 (2004).

89. Deng, Z. B. et al. Adipose tissue exosome-like vesicles mediate activation of macrophage-induced insulin resistance. *Diabetes* 58, 2498-2505 (2009).

90. Liu, Y. et al. Contribution of MyD88 to the tumor exosome-mediated induction of myeloid derived suppressor cells. *Am J Pathol* 176, 2490-2499.

91. Zhao, S. & Fernald, R. D. Comprehensive algorithm for quantitative real-time polymerase chain reaction. *J Comput Biol* 12, 1047-1064 (2005).

It will be understood that various details of the presently disclosed subject matter can be changed without departing from the scope of the subject matter disclosed herein.

What is claimed is:

1. A method of delivering a therapeutic agent to a mammal, the method comprising administering to the mammal an exosomal composition comprising a therapeutic agent encapsulated by an isolated exosome derived from a plant; wherein the exosome is isolated from the juice of a fruit of the plant.

2. The method of claim 1, wherein the therapeutic agent is a phytochemical agent.

3. The method of claim 2, wherein the phytochemical agent is selected from the group consisting of curcumin, resveratrol, baicalein, equol, fisetin, and quercetin.

4. The method of claim 1, wherein the therapeutic agent is a chemotherapeutic agent.

5. The method of claim 4, wherein the chemotherapeutic agent is selected from the group consisting of retinoic acid, 5-fluorouracil, vincristine, actinomycin D, cisplatin, docetaxel, doxorubicin, and paclitaxel.

6. The method of claim 1, wherein the therapeutic agent is a Stat3 inhibitor.

7. The method of claim 1, wherein the therapeutic agent is an siRNA.

8. The method of claim 1, wherein the therapeutic agent is a microRNA.

9. The method of claim 1, wherein the exosomal composition binds to a target cell or tissue.

10. The method of claim 1, wherein the exosomal composition further comprises a pharmaceutically-acceptable vehicle, carrier, or excipient.

11. The method of claim 1, wherein the exosomal composition is formulated for intranasal, oral, or intratumoral administration.

12. The method of claim 1, wherein the exosomal composition is administered intranasally.

13. The method of claim 1, wherein the exosomal composition is administered orally.

* * * * *